US007063966B2

(12) United States Patent
Shankar et al.

(10) Patent No.: US 7,063,966 B2
(45) Date of Patent: Jun. 20, 2006

(54) CHIMERIC G PROTEIN COUPLED RECEPTORS

(75) Inventors: Geetha Shankar, Menlo Park, CA (US); Jason N. Munning, San Francisco, CA (US); Juliet V. Spencer, Foster City, CA (US)

(73) Assignee: SRI International, Menlo Park, CA (US)

( * ) Notice: Subject to any disclaimer, the term of this patent is extended or adjusted under 35 U.S.C. 154(b) by 0 days.

(21) Appl. No.: 09/904,099

(22) Filed: Jul. 11, 2001

(65) Prior Publication Data

US 2003/0119092 A1    Jun. 26, 2003

(51) Int. Cl.
    C07K 17/705    (2006.01)
    C07K 19/00     (2006.01)
    C12N 15/62     (2006.01)

(52) U.S. Cl. .................. 435/69.7; 435/7.21; 435/252.3; 435/320.1; 530/350; 536/23.4

(58) Field of Classification Search ............... 435/7.21, 435/69.7; 530/300; 536/23.4
    See application file for complete search history.

(56) References Cited

FOREIGN PATENT DOCUMENTS

WO    WO 00/56135    9/2000

OTHER PUBLICATIONS

Ancellin et al. Differential Pharmacological Properties and Signal Transduction of Sphingosine 1-phosphate Receptors EDG-1, EDG-3, and EDG-5. Jul. 2, 1999, J. Bio. Chem. 274(27):18997-19002.*
Conway et al. Chimeric Melatonin mt1 and Melatonin-related Receptors. Jul. 7, 2000. J. Biol. Chem. 275(27):20602-20609.*
Schoth et al. Chimeric MC! and MC3 Receptors: Identification of Domains Participating in Binding of Melanocyte-Stimulating Hormone Peptides. 1998. Mol. Pharm. 54:154-161.*
Wu et al. First Intracellular Loop of the Human Cholecystokinin-A Receptor is Essential for Cyclic AMP Signalling in Transfected HEK-293 Cells. J. Biol. Chem. 272(14):9037-9042.*
Meng et al. Mapping the Receptor Domains Critical for the Binding Selectivity of delta-opiod Receptor Ligands. 1996. Euro. J. Pharm. 311:285-292.*
Holtzmann et al. Critical Contributions of Amino-terminal Extracellular Domains in Agonist Binding and Activation of Secretin and Vasoactive Intestinal Polypeptides Receptors. Jun. 16, 1995. J. Biol. Chem. 270(24):14394-14398.*
Takagi et al. Structural Basis of G Protein Specificity of Human Endothelin Receptors. Apr. 28, 1995. 270(171):10072-10078.*
Buggy et al. Glucagon-Glucagon-like Peptide 1 Receptor Chimeras Reveal Domains That Determine Specificity of Glucagon Binding. Mar. 31, 1995. J. Biol. Chem. 270(13):7474-7478.*
Kim et al. Random Chimeragenesis of G-protein-coupled Receptors. Nov. 18, 1994. J. Biol. Chem. 269(46):28724-28731.*
Gether et al. Chimeric NK1 (SubstanceP)/NK3 (Neurokinin B) Receptors. Apr. 15, 1993. J. Biol. Chem. 268(11):7893-7898.*
MacLennan et al., 1994, "Cloning and Characterization of a putative G-Protein Coupled Receptor Potentially Involved in Development," *Molecular and Cellular Neuroscience* 5(3), 201-209.
Medici et al., 1997, "Efficient Signal Transduction By A Chimeric Yeast-Mammalian G Protein α subunit Gpa1-Gsα Covalently Fused to the Yeast Receptor Ste2," *EMBO J* 16, 7241-7249.
Sambrano et al., 1999, "The Carboxyl Tail of Protease-Activated Receptor-1 Is Required for Chemotaxis," *Journal of Biological Chemistry* 274(29), 20178-20184.
Jewell-Motz et al., 2000, "α2A/α2C-Adrenergic Receptor Third Loop Chimera Show That Agonist Interaction With Receptor Subtype Backbone Establishes G Protein-Coupled Receptor Kinase Phosphorylation," *Journal of Biological Chemistry* 275(37), 28989-28993.
Nanevicz et al., 1996, "Thrombin Receptor Activating Mutations," *Journal of Biological Chemistry* 271(2), 702-706.
Cypess et al., 1999, "Two Cytoplasmic Loops of the Glucagon Receptor Are Required to Elevate cAMP or Intracellular Calcium," *Journal of Biological Chemistry* 274(27), 19455-19464.
Hla, Timothy., 2001, "Sphingosine 1-Phosphate Receptors," *Prostaglandins & Other Lipid Mediators* 64 (2001) 135-142.
Weber,Michael-Wolf, 1999, "Ion Currents of *Xenopus laevis* Oocyte: State of the Art," *Biochimica et Biophysica Acta* 1421, 213-233.
Bandoh et al., 2000,"Lysophosphatidic acid (LPA) Receptors of the EDG Family Are Differentially Activated by LPA Species," *FEBS Letters* 478 (2000) 159-165.
van Koppen et al., 1996,"Activation of a High Affinity Gi Protein-Coupled Plasma Membrane Receptor By Sphingosine-1-Phosphate," Journal of Biological Chemistry 271(4) 2082-2087.

(Continued)

*Primary Examiner*—John Ulm
(74) *Attorney, Agent, or Firm*—Morgan, Lewis & Bockius LLP

(57)    ABSTRACT

The present invention provides chimeric Edg receptors, useful as components of an assay system. The present invention also provide methods of screening for compounds that bind a chimeric Edg receptor, for example, by contacting a chimeric Edg receptor with a compound and detecting a change in chimeric Edg receptor-mediated activity such as calcium mobilization.

17 Claims, 5 Drawing Sheets

OTHER PUBLICATIONS

Figure 1A:
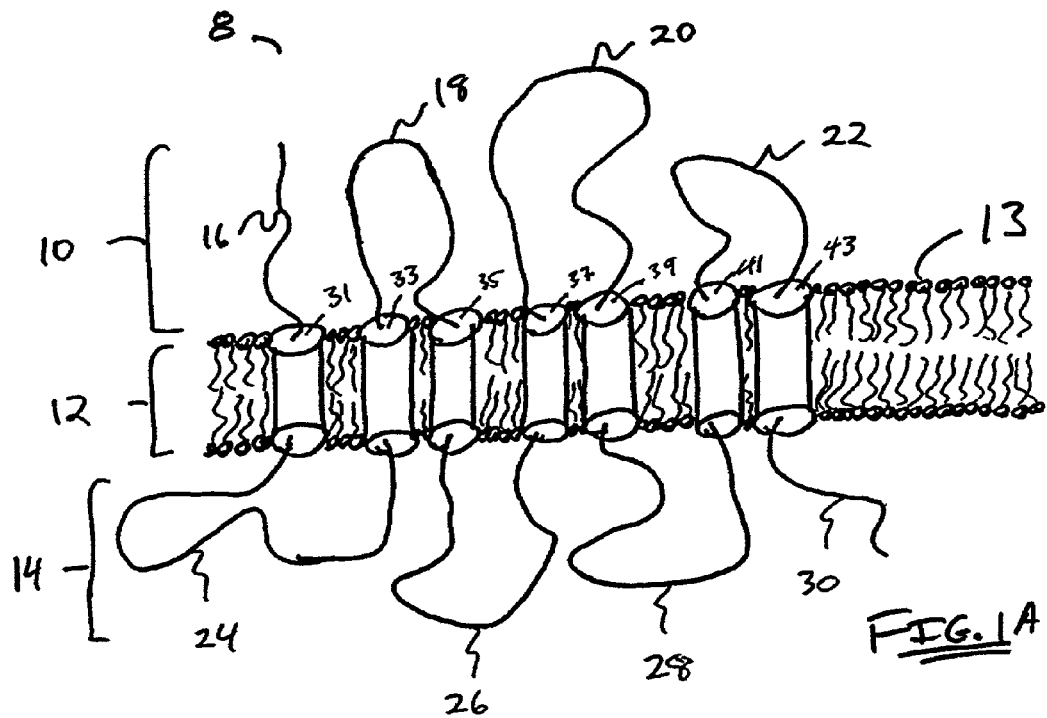

Van Brocklyn et al., 1998,"Dual Actions of Sphingosine-1-Phosphate: Extracellular Through the Gi-Coupled Receptor Edg-1 and Intracellular to Regulate Proliferation and Survival," *Journal of Cell Biology* 142(1) 229-240.

Gether, Ulrik., 2000,"Uncovering Molecular Mechanisms Involved In Activation of G Protein-Coupled Receptors," Endocrine Reviews 21, 90-113.

Berridge et al., 2000,"The Versatility and Universality Of Calcium Signalling," *Nature Reviews* 1, 11-21.

Moolenaar et al., 1997,"Lysophosphatidic acid: G-protein Signalling and Cellular Responses," Current Opinion in Cell Biology 9, 168-173.

Parill et al., 2000,"Identification of Edg1 Receptor Residues That Recognize Sphingosine 1-Phosphate," *Journal of Biological Chemistry* 275 (50), 39,379-39,384.

An et al., 1998,"Characterization of a Novel Subtype of Human G Protein-Coupled Receptor for Lysophoshatidic Acid," *Journal of Biological Chemistry* 273 (14), 7906-7910.

Bandoh et al., 1999,"Molecular Cloning and Characterization of a Novel Human G-Protein-Coupled Receptor, EDG7, for Lysophosphatidic Acid," *Journal of Biological Chemistry* 274(39), 27,776-27,785.

Kolakowski, Lee F., 1994,"GCRDb: A G-Protein-Coupled Receptor Database," *Receptors and Channels* 2, 1-7.

Verrall et al.,1997,"The Thrombin Receptor Second Cytoplasmic Loop Confers Coupling to Gq-Like G Proteins in Chimeric Receptors," *Journal of Biochemistry* 272(11) 6898-6902.

Im et al., Dec. 6, 2000, GenBank Accession No.: AF233365.

Yamaguchi et al., Jan. 8, 1997, GenBank Accession No.: X83864.

Graeler, M.H., Nov. 17, 1998, GenBank Accession No.: AJ000479.

Tigyi et al., Mar. 15, 2000, GenBank Accession No.: AF317676.

Moolenaar et al., Feb. 4, 1998, GenBank Accession No.: U78192.

Bandoh et al., Aug. 17, 2000, GenBank Accession No.: AF233092.

An et al., Jul. 29, 1998, GenBank Accession No.: AF011466.

MacLennan et al., Jan. 1, 1999, GenBank Accession No.: AF034780.

Bandoh et al., Sep. 25, 1999, GenBank Accession No.: AF127138.

International Search Report Corresponding to PCT/US02/22346, Oct. 21, 2002.

Hammerland et al., "Domains determining ligand specificity for $Ca^{2+}$ receptorts", Molecular Pharmacology, (1999), 55:642-648.

Jutta et al., "Preservation of $G_1$ coupling of a chimeric $EP_3$/I-type prostaglandin (IP) receptor", Biochemical Pharmacology, (1999), 58:471-476.

Kobilka et al., "Chimeric $\alpha_2$-, $\beta_2$-adrenergic receptors: delineation of domains involved in effector coupling and ligand binding specificity", Science, (1988) 240:1310-1316.

Liu et al., "Ligand-induced trafficking of the sphingosine-1-phosphate receptor EDG-1", Molecular Biology of the Cell, (1999), 10:1179-1190.

Songzhu et al., "Signaling mechanisms and molecular characteristics of G protein-coupled receptors for lysophosphatidic acid and sphingosine 1-phosphate", Journal of Cellular Biochemistry Supplements, (1998), Suppl 30, 31:147-157.

* cited by examiner ively, detection of changes in intracellular calcium in whole cells, in real-time, is feasible and affordable. Advances in hardware, fluorescent detection tools and sensitive cameras, have further enabled assays for screening compounds in drug discovery programs in a high throughput format (Grynkiewicz et al., *J. Biol. Chem.* 260:3440–3450; Mason et al., in "Fluorescent and Luminescent probes for Biological Activity"; ed. W. T. Mason; pp 161–195; Academic Press, London). There are many advantages to using such an assay: (i) the response is rapid (milliseconds to seconds); (ii) the response is transient; (iii) the response can be measured in whole, live cells and not just cell membranes and (iv) the response is a measure of receptor activation, rather than just receptor binding. Modulation of such a response is therefore biologically relevant, and can have long-term consequences to the behavior of the cell.

CHIMERIC G PROTEIN COUPLED RECEPTORS

1. FIELD OF THE INVENTION

The present invention relates to novel chimeric G protein receptors such as novel chimeric Edg receptors.

2. BACKGROUND OF THE INVENTION

G-protein coupled receptors ("GPCRs") are integral membrane proteins that relay signals from cell surface receptors to intracellular effectors. To date, over 1000 different GPCRs have been identified (see, e.g., Gether, 2000, *Endocrine Reviews* 21:90–113; Kolakowski, 1994, *Receptor Channels* 2:1–7). GPCRs respond to a broad range of extrracellular signals including, for example, hormones, neurotransmitters, chemokines, odorants and light (see, e.g., Buneman & Hosey, 1999, *J. Physiol.* 517.1:5–23). They play vital roles in fundamental cell processes including growth, differentiation and survival. Currently, over 25% of drugs currently on the market target GPCRs. These drugs include antipsychotics, antihistamines, antihypertensives, anti-migraine drugs, anti-ulcer drugs and analgesics.

They typically span the membrane seven times and comprise an extracellular domain, a transmembrane domain, and a cytoplasmic domain. The transmembrane domain usually comprises seven transmembrane helices. Members of this superfamily couple to heterotrimeric intracellular G proteins comprising α, β and γ subunits. In its inactive state the Gα subunit binds GDP. When the receptor is activated, it physically associates with a G-protein and catalyzes the exchange of GTP for bound GDP in its Gα subunit. Following receptor activation, the βγ subunits, which bind to each other very tightly, as well as the GTP-Gα subunit dissociate from the receptor and from each other. All three subunits, the activated α and the free βγ, interact with and activate specific downstream cellular effectors, depending on the nature of the receptor-ligand interaction. Intrinsic GTPase activity in the Gα subunit converts it to the inactive GDP-bound form, and reassociation of the heterotrimeric complex restores the receptor to its resting state.

Currently, 17 Gα-subunits, 5 Gβ subunits and 12 Gγ subunits have been identified and described (Dhanasekaran et al., *Oncogene* 1998 17:1383–1394; Hepler and Gilman, *Trends Biochem. Sci.* 1992 17:383–387; Strathman et al., *Proc. Natl. Acad. Sci.* 1991 86:7407–7409). Although signaling heterogeneity is derived from the various combinations of α, β and γ subunits, G-proteins are classified into four distinct classes based on the sequence similarity of their Gα subunits (subunits that are >50% similar are typically grouped in the same class): (a) Gαs (coupled to stimulation of adenylyl cyclase activity and cAMP formation); (b) Gαi (coupled to inhibition of adenylyl cyclase activity and suppression of cAMP formation; (c) Gαq (coupled to activation of phospholipase C (PLC) and mobilization of intracellular calcium); and (d) Gα12: (coupled to activation of downstream effectors such as rac, rho; coupled to changes in intracellular cytoskeletal elements; not clearly understood).

According to conventional techniques, the activities of only a subset of the known GPCRs can be readily measured in a high throughput manner. In particular, those GPCRs that couple with the Gαq effector protein typically generate a calcium signal, mediated by various calcium-mobilizing messengers, that can be measured in a readily accessible assay. In particular, membrane-permeant fluorescent dyes, such as Fura-2 AM, and Fluo-4 AM, have a high affinity and specificity for ions such as calcium and undergo a significant shift in emitted wavelength when bound to calcium. With such dyes, detection of changes in intracellular calcium in whole cells, in real-time, is feasible and affordable.

Although the calcium assay is very suitable for high-throughput screens, it suffers at least one major disadvantage: it can only be applied to receptors that are coupled to second messenger pathways that involve changes in intracellular calcium. For the GPCR superfamily, this technique is restricted to the Gαq-coupled receptors. Traditional methods for assaying the remaining GPCRs are labor and time intensive and cannot be readily utilized in a high throughput manner. These include binding assays, cAMP detection, and reporter gene techniques, and typically involve significantly more time and effort than a calcium mobilization assay. Further, binding assays are not whole cell assays and therefore do not necessarily have a biologically relevant read-out. In addition, cAMP assays are not as rapid and transient as calcium assays. Furthermore, reporter gene techniques are significantly more time intensive, not always robust and reproducible and measure responses that are much further downstream of receptor activation than calcium mobilization. These responses can therefore be prone to receptor-independent cellular effects that can be misinterpreted as receptor-dependent effects. Therefore, new compositions and methods are needed to facilitate high throughput measurement of the activities of a broad range of GPCRs.

3. SUMMARY OF THE INVENTION

In one aspect, the present invention provides novel chimeric G protein coupled receptors ("GPCRs"). The novel chimeric GPCRs are designed from a first GPCR and typically incorporate a portion of a second GPCR. Preferred chimeric GPCRs retain the native ligand binding properties of the first GPCR and are readily detectable in high throughput assays because they comprise a portion of the second GPCR.

In one embodiment, a chimeric GPCR of the invention comprises the extracellular domain of a first GPCR, the transmembrane domain of the first GPCR and a chimeric intracellular domain. In certain preferred embodiments, the chimeric intracellular domain comprises at least two strands having the polypeptide sequences of a corresponding strand of a second GPCR. The other strands of the chimeric intracellular domain can have the polypeptide sequence of a corresponding strand in the first GPCR, the polypeptide sequence of a corresponding strand in another GPCR, or any other polypeptide sequence. In certain embodiments, all strands of the chimeric intracellular domain have the polypeptide sequences of corresponding strands in the second GPCR. In another embodiment, a chimeric GPCR of the invention comprises the extracellular domain of a first GPCR, the transmembrane domain of the second GPCR and an intracellular domain comprising at least two strands having the polypeptide sequences of the corresponding strands of the second GPCR. The other strands of the intracellular domain can have the polypeptide sequence of a corresponding strand in the second GPCR, a corresponding strand in another GPCR or any other polypeptide sequence. In yet another embodiment, a chimeric GPCR of the invention comprises the extracellular domain of a first GPCR, the transmembrane domain of a second GPCR and the intracellular domain of the second GPCR.

In another embodiment, a chimeric GPCR of the invention is a chimeric Edg receptor comprising the extracellular domain of a first Edg receptor, the transmembrane domain of the first Edg receptor and a chimeric intracellular domain. The chimeric intracellular domain comprises at least one strand having the polypeptide sequence of a corresponding strand of a second Edg receptor. The other strands of the chimeric intracellular domain can have the polypeptide sequence of a corresponding strand in the first Edg receptor, the polypeptide sequence of a corresponding strand in another Edg receptor, the polypeptide sequence of a corresponding strand in another GPCR or any other polypeptide sequence. In certain embodiments, all strands of the chimeric intracellular domain have the polypeptide sequences of corresponding strands in the second Edg receptor.

As illustrated in FIG. 1, GPCRs typically possess extracellular domains ("ECDs") 10, intracellular domains ("ICDs") 14 and transmembrane domains ("TMDs") 12. The ECD and ICD of a GPCR may each comprise four strands, and the TMD of a GPCR may comprise seven strands. A strand is a contiguous stretch of amino acids within a domain of a GPCR. For instance, the strands of ECD 10 include amino-terminal strand 16, loop 18, loop 20 and loop 22. The strands of ICD 14 include first intracellular loop 24, second intracellular loop 26, third intracellular loop 28 and carboxy-terminal strand 30. Typically, a strand is linked to another domain of the GPCR. For instance, first intracellular loop 24 is linked to TMD helix 31 and to TMD helix 33.

While not intending to be bound by any particular theory, the ECD and/or TMD of a GPCR can bind the ligand of the GPCR to initiate signaling by the receptor. The ICD of the GPCR can interact with a Gα protein to initiate intracellular signaling. Native GPCRs selectively interact with certain Gα proteins to trigger specific cellular responses. The responses depend on the identity of the Gα protein. For instance, Gαq stimulates phospholipase C activity and the mobilization of intracellular calcium. Several other Gα proteins, including, but not limited to, Gαs, Gαi, Gα12/13 might trigger other intracellular responses. A chimeric GPCR designed from a first GPCR that couples with one of these Gα proteins can trigger calcium mobilization if, in the chimeric GPCR, at least one strand of its ICD is replaced with a corresponding strand from a second GPCR that couples with a Gαq protein according to the present invention. The resulting chimeric GPCR can then easily be assayed, for instance, by measuring calcium mobilization.

Thus, particularly useful chimeric GPCRs include those wherein one or more ICD strands are replaced with corresponding strands from a Gαq coupled GPCR. For instance, the native Edg 1 receptor, a GPCR that has been linked to endothelial differentiation, typically couples with a Gαi protein and inhibits cAMP formation. A chimeric GPCR can be designed from the primary sequence of the Edg 1 receptor and one or more ICD strands from a Gαq coupled GPCR, e.g. Edg 3, to generate a chimeric Edg 1 receptor that triggers calcium mobilization in the appropriate cell type.

The chimeric ICD strands may be linked to the remainder of the chimeric G protein coupled receptor via virtually any type of linkage known to those of skill in the art for linking peptide or polypeptide moieties together. Typically, the linkage will be covalent, and may include an optional linker or spacer molecule. In embodiments in which the chimeric G protein coupled receptor will be expressed using biological systems, the chimeric ICD strands are fused either directly or through a peptide linker or spacer to the amino- or carboxy-termini of adjacent TMD helices. In embodiments in which the chimeric G protein coupled receptor is prepared synthetically or semisynthetically, the chimeric strands may be linked to the amino- or carboxy-termini of adjacent TMD helices using virtually any linkage chemistry that does not destroy the integrity of the entire chimeric G protein coupled receptor. The linkage may be mediated by way of a linker or spacer molecule, which may be biological or non-biological in nature.

In another aspect, the present invention provides nucleic acids for expressing the chimeric GPCRs of the invention. The nucleic acid may be an RNA or a DNA having a sequence that encodes the chimeric GPCR operatively linked to a regulatory sequence that directs or effects expression. In a particularly useful embodiment, the nucleic acid is a DNA expression vector. Such vectors generally comprise a promoter operatively linked to a polynucleotide that encodes the chimeric GPCR.

In still another aspect, the present invention provides cells capable of expressing a chimeric GPCR. The cells of the invention generally comprise a nucleic acid capable of expressing a chimeric GPCR. The cells can be prokaryotic or eukaryotic, and the cells can be stably or transiently transfected with the nucleic acid.

In yet another aspect, the present invention provides methods of expressing a chimeric GPCR. The methods comprise expressing a nucleic acid encoding a chimeric GPCR of the invention and recovering the chimeric GPCR. In a particularly convenient embodiment, host cells comprising a nucleic acid capable of expressing the chimeric GPCR are cultured under conditions which permit expression and the expressed chimeric GPCR is recovered from the culture, e.g., in a purified form or as part of a membrane preparation.

In another aspect, the present invention provides methods of screening for compounds that bind and/or modulate the activity of a first GPCR. In embodiments of these methods, a chimeric GPCR designed from a first GPCR and comprising a chimeric ICD is contacted with a test compound. The cell is then assayed for a detectable signal that indicates compound binding and/or modulation of the activity of the chimeric GPCR. The signal can be, for instance, a signal produced by a downstream effector of the second GPCR.

The chimeric GPCRs of the invention will find use in virtually any type of method in which the signaling and/or G protein coupling of a GPCR can be altered. For example, the chimeric GPCRs are useful in a high-throughput screening assay to identify compounds that bind the polypeptide. The chimeric GPCRs of the invention thus enable high throughput uses that are not achievable with the first GPCR from which they are designed.

4. BRIEF DESCRIPTION OF THE FIGURES

Figure 1B:
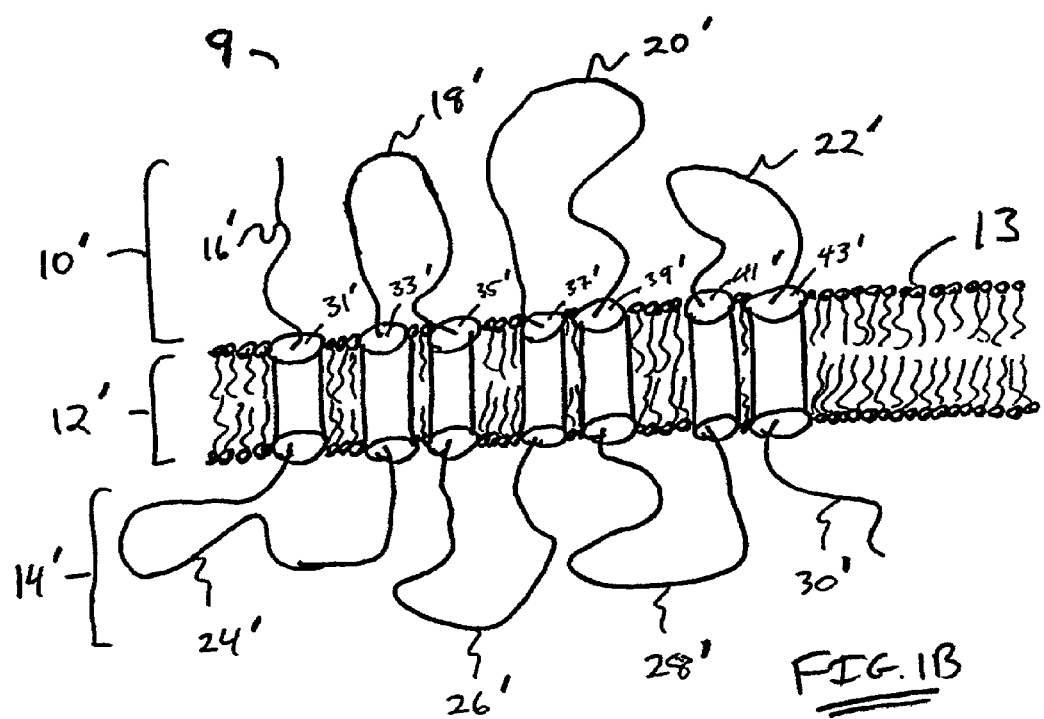
Figure 2:
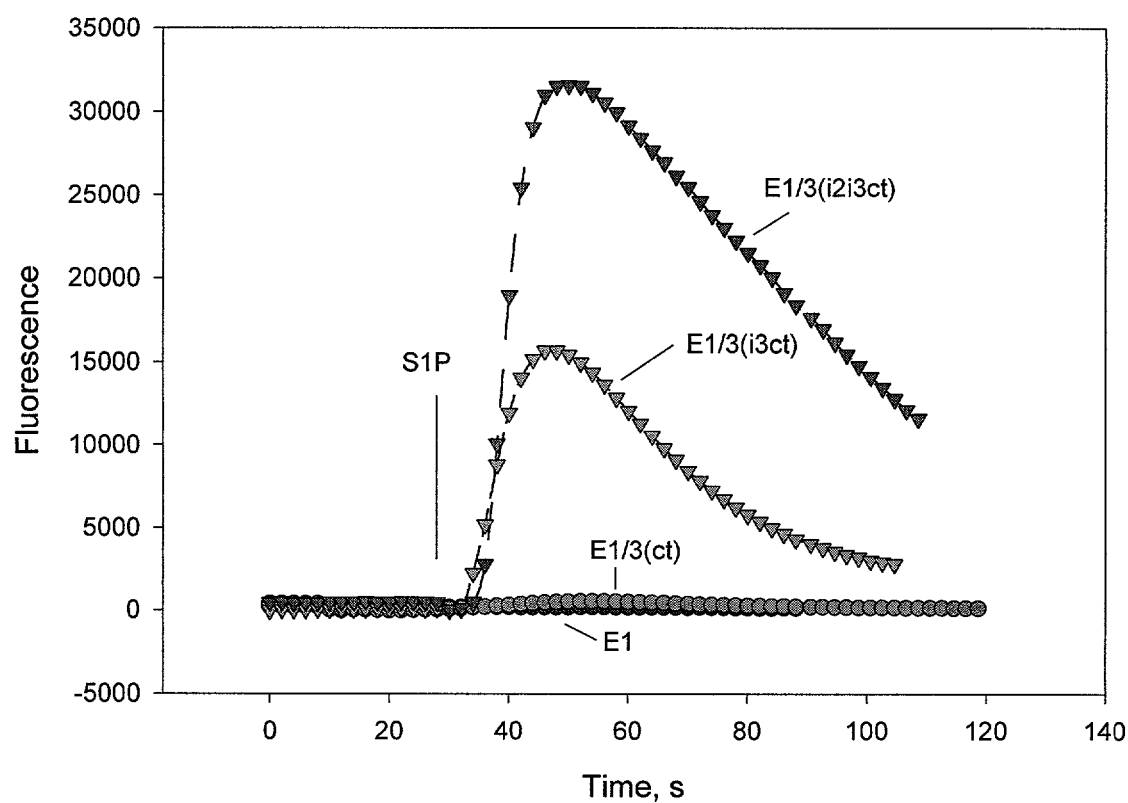
Figure 3:
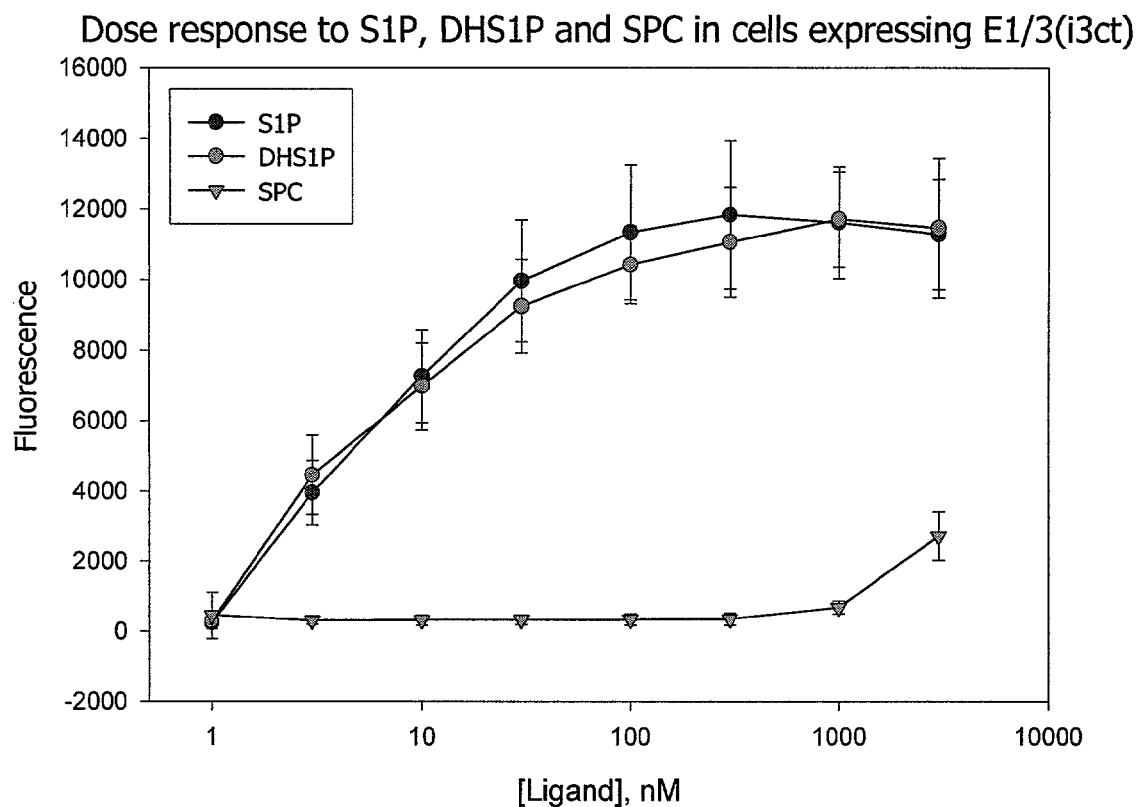
Figure 4:
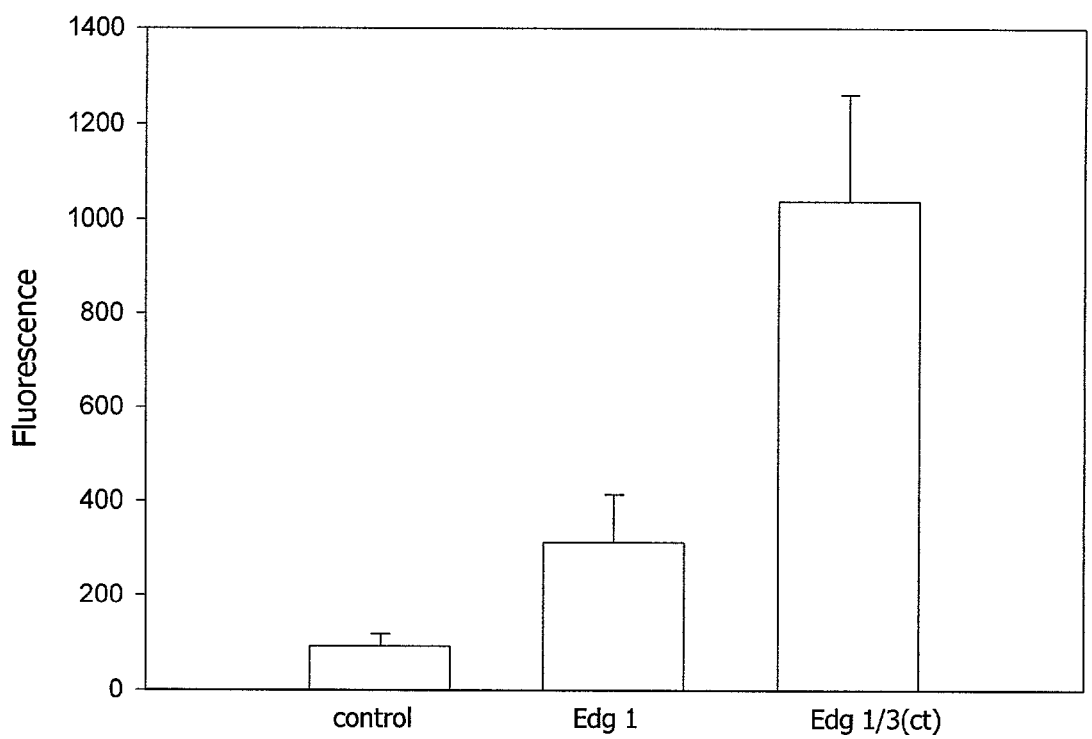
Figure 5:
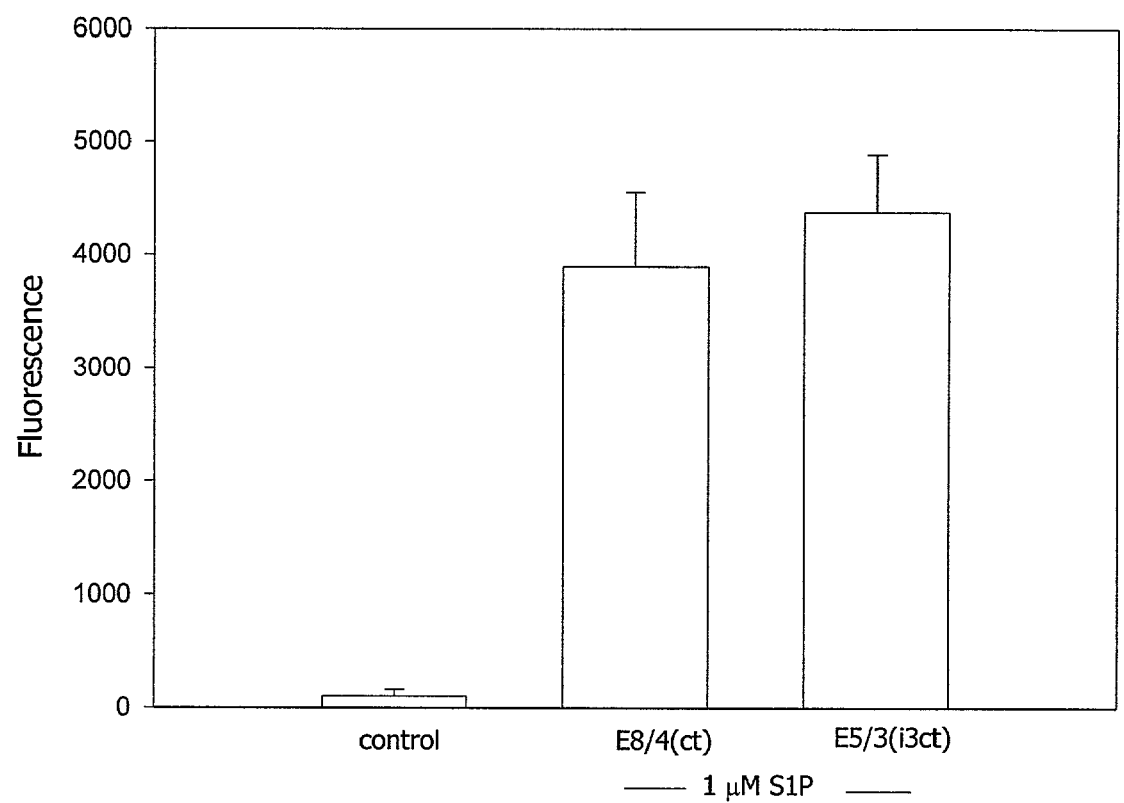

FIG. 1A provides a schematic representation of an exemplary G protein coupled receptor;

FIG. 1B provides a schematic representation of a chimeric GPCR of the invention designed from the native GPCR of FIG. 1A;

FIG. 2 provides intracellular calcium mobilization by chimeric GPCRs of the invention;

FIG. 3 provides the dose response of intracellular calcium mobilization by a chimeric GPCR of the invention;

FIG. 4 provides intracellular calcium mobilization by an Edg 1/3(ct) chimera; and FIG. 5 provides intracellular calcium mobilization by Edg8/4(ct) and Edg5/3(i3ct) chimeras.

5. DETAILED DESCRIPTION OF THE PREFERRED EMBODIMENTS

The present invention provides novel compositions designed from a first G protein coupled receptor that mimic or possess one or more of the biological activities of a second G protein coupled receptor. The compositions can be used, for instance, to adapt a first G protein coupled receptor to a convenient high throughput method of screening.

5.1 Abbreviations

The amino acid notations used herein for the twenty genetically encoded L-amino acids are conventional and are as follows:

TABLE 1

| Amino Acid | One-Letter Abbreviation | Three Letter Abbreviation |
|---|---|---|
| Alanine | A | Ala |
| Arginine | R | Arg |
| Asparagine | N | Asn |
| Aspartic acid | D | Asp |
| Cysteine | C | Cys |
| Glutamine | Q | Gln |
| Glutamic acid | E | Glu |
| Glycine | G | Gly |
| Histidine | H | His |
| Isoleucine | I | Ile |
| Leucine | L | Leu |
| Lysine | K | Lys |
| Methionine | M | Met |
| Phenylalanine | F | Phe |
| Proline | P | Pro |
| Serine | S | Ser |
| Threonine | T | Thr |
| Tryptophan | W | Trp |
| Tyrosine | Y | Tyr |
| Valine | V | Val |

As used herein, unless specifically delineated otherwise, the three-letter amino acid abbreviations designate amino acids in the L-configuration. Amino acids in the D-configuration are preceded with a "D-." For example, Arg designates L-arginine and D-Arg designates D-arginine. Likewise, the capital one-letter abbreviations refer to amino acids in the L-configuration. Lower-case one-letter abbreviations designate amino acids in the D-configuration. For example, "R" designates L-arginine and "r" designates D-arginine.

Unless noted otherwise, when polypeptide sequences are presented as a series of one-letter and/or three-letter abbreviations, the sequences are presented in the N->C direction, in accordance with common practice.

The abbreviations used throughout the specification to refer to nucleic acids comprising specific nucleobase sequences are the conventional one-letter abbreviations. Thus, when included in a nucleic acid, the naturally occurring encoding nucleobases are abbreviated as follows: adenine (A), guanine (G), cytosine (C), thymine (T) and uracil (U). Also, unless specified otherwise, nucleic acid sequences that are represented as a series of one-letter abbreviations are presented in the 5'->3' direction.

5.2 Definitions

As used herein, the following terms shall have the following meanings:

"Genetically Encoded Amino Acid" refers to L-isomers of the twenty amino acids that are defined by genetic codons. The genetically encoded amino acids are the L-isomers of glycine, alanine, valine, leucine, isoleucine, serine, methionine, threonine, phenylalanine, tyrosine, tryptophan, cysteine, proline, histidine, aspartic acid, asparagine, glutamic acid, glutamine, arginine and lysine.

"Genetically Non-Encoded Amino Acid" refers to amino acids that are not defined by genetic codons. Genetically non-encoded amino acids include derivatives or analogs of the genetically-encoded amino acids that are capable of being enzymatically incorporated into nascent polypeptides using conventional expression systems, such as selenomethionine (SeMet) and selenocysteine (SeCys); isomers of the genetically-encoded amino acids that are not capable of being enzymatically incorporated into nascent polypeptides using conventional expression systems, such as D-isomers of the genetically-encoded amino acids; L- and D-isomers of naturally occurring α-amino acids that are not defined by genetic codons, such as α-aminoisobutyric acid (Aib); L- and D-isomers of synthetic α-amino acids that are not defined by genetic codons; and other amino acids such as β-amino acids, γ-amino acids, etc. In addition to the D-isomers of the genetically-encoded amino acids, exemplary common genetically non-encoded amino acids include, but are not limited to, norleucine (Nle), penicillamine (Pen), N-methylvaline (MeVal), homocysteine (hCys), homoserine (hSer), 2,3-diaminobutyric acid (Dab) and ornithine (Orn). Additional exemplary genetically non-encoded amino acids are found, for example, in *Practical Handbook of Biochemistry and Molecular Biology*, 1989, Fasman, Ed., CRC Press, Inc., Boca Raton, Fla., pp. 3–76 and the various references cited therein.

"TMD Strand" or "TMD Helix" refer interchangeably to an individual polypeptide strand of an integral membrane protein, whether helical or non-helical in structure, that traverses the cell membrane. For example, strands 31, 33, 35, 37, 39, 41 and 43 of the G protein coupled receptor illustrated in FIG. 1A are each TMD strands or TMD helices.

"Transmembrane Domain" or "TMD" refers collectively to all strands of an integral membrane protein that traverse the cell membrane. For example, the TMD of the G protein coupled receptor illustrated in FIG. 1A comprises strands 31, 33, 35, 37, 39, 41 and 43 (illustrated as cylinders in FIG. 1A).

"Intracellular Strand" refers to a contiguous stretch of amino acids of an integral membrane protein that reside on the interior (intracellular) side of the cell. For example, in the G protein coupled receptor illustrated in FIG. 1A, preferred intracellular strands include first intracellular loop 24, second intracellular loop 26, third intracellular loop 28 and carboxy terminal strand 30.

"Intracellular Domain" or "ICD" refers collectively to all strands of an integral membrane protein that reside on the interior (intracellular) side of the cell. For example, the ICD of the G protein coupled receptor illustrated in FIG. 1A comprises first intracellular loop 24, second intracellular loop 26, third intracellular loop 28 and carboxy terminal strand 30.

"Extracellular Strand" refers to a contiguous stretch of amino acids of an integral membrane protein that reside on the exterior (extracellular) side of the cell. For example, in the G protein coupled receptor illustrated in FIG. 1A, preferred extracellular strands include first extracellular loop 18, second extracellular loop 20, third extracellular loop 22 and amino terminal strand 16.

"Extracellular Domain" or "ECD" refers collectively to all strands of an integral membrane protein that reside on the exterior (extracellular) side of the cell. For example, the ECD of the G protein coupled receptor illustrated in FIG. 1A comprises first extracellular loop 18, second extracellular loop 20, third extracellular loop 22 and amino terminal strand 16.

"Function" or "Activity" refers to a biological activity of a molecule of the invention. The biological activity is any activity recognized by those of skill in the art. For instance, biological activities include ligand binding, antibody binding, receptor signaling, other intermolecular interactions, immunogenicity and other biological activities recognized by those of skill in the art. In particular, when a chimeric GPCR retains or mimics the function or activity of an integral membrane protein, the chimeric GPCR should mimic or retain at least one biological activity of the integral membrane protein. A preferred function or activity of a chimeric GPCR of the invention is the ability of the chimera to trigger the mobilization of intracellular calcium.

5.3 Chimeric GPCRs

The chimeric GPCRs of the invention may be designed from any G protein coupled receptor. Examples of G protein coupled receptors that can be used to design chimeric GPCRs include, by way of example and not limitation, GPCRs in the β-adrenergic, thrombin, secretin and VPAC families of receptors. Specific examples of GPCRs that can be used for the design of a chimeric GPCR according to the present invention include, for example, Edg receptors such as Edg 1, Edg 2, Edg 3, Edg 4, Edg 5, Edg 6, Edg 7 and Edg 8. Other examples include Gαi-coupled receptors such as cannabinoid receptors, adenosine receptors; Gαs-coupled receptors such as glucagon receptors, GnRH receptors; Gα12-coupled receptors such as thromboxane receptors, and neurokinin-1 receptors.

Referring to FIG. 1A, a typical G protein coupled receptor 8 from which a chimeric GPCR may be designed comprises an ECD 10, a TMD 12 (illustrated embedded in membrane 13) and an ICD 14. TMD 12 is composed of seven helices—TMD helices 31, 33, 35, 37, 39, 41 and 43 (illustrated as cylinders). ECD 10 is composed of four strands—amino terminal strand 16, first extracellular loop 18, second extracellular loop 20 and third extracellular loop 22. ICD 14 is composed of four strands—first intracellular loop 24, second intracellular loop 26, third intracellular loop 28 and carboxy termignal strand 30.

The starting and ending points of the various strands of GPCR 8 can be determined according to a variety of methods known to those of skill in the art. For instance, the boundaries of the strands of many GPCRs are well known in the art. In instances where such boundaries are not known, they can be readily ascertained from the sequence of GPCR 8 in conjunction with hydropathy analyses or plots (see, e.g., Kyte & Doolittle, 1982, J. Mol. Biol. 157:105–132), as well as other methods, such as sequence alignments, as are known in the art.

In one embodiment, a chimeric GPCR of the invention 9 may be designed from integral membrane protein 8. Referring to FIG. 1B, to design a chimeric GPCR 9 of the invention from first GPCR 8, the ICD 14 of first GPCR 8 is replaced with chimeric ICD 14'. Chimeric GPCR 9 thus comprises ECD 10', TMD 12' and chimeric ICD 14'. Chimeric ICD 14' is described in detail below. In chimeric GPCR 9, ECD 10' typically corresponds to ECD 10 of first GPCR 8, and TMD 12' typically corresponds to TMD 12 of first GPCR 8.

In another embodiment, a chimeric GPCR of the invention 9 may be designed from integral membrane protein 8. Referring to FIG. 1B, to design a chimeric GPCR 9 of the invention from first GPCR 8, the ICD 14 of first GPCR 8 is replaced with chimeric ICD 14', and the TMD 12 of first GPCR 8 is replaced with chimeric TMD 12'. Chimeric GPCR 9 thus comprises ECD 10', chimeric TMD 12' and chimeric ICD 14'. Chimeric ICD 14' is described in detail below. Chimeric TMD 12' can comprise one or more of the TMD strands, or a portion thereof, of a second GPCR. In chimeric GPCR 9, ECD 10' typically corresponds to ECD 10 of first GPCR 8. Preferably, in such embodiments the first GPCR is one in which its native ligand binds the ECD and does not significantly bind the TMD, e.g. the metabotropic glutamate receptors and the metabotropic γ-amino butyric acid receptors (see, e.g., Gether, 2000, *Endocrine Reviews* 21:90–113).

The chimeric GPCRs of the invention can be used, for instance, to alter the downstream signaling properties of first GPCR 8. While not intending to be bound by any particular theory of operation, native GPCRs can function by transducing signals from a bound ligand on the surface of a cell to downstream effectors within the cell. GPCRs generally couple with one or more specific Gα proteins to initiate the intracellular signaling process. The type of Gα protein to which the GPCR couples typically determines the character of the response to signaling of the GPCR. Surprisingly, the chimeric GPCRs of the present invention display altered coupling properties. By replacing the appropriate ICD strand or strands in a first GPCR with a corresponding strand or strands of a second GPCR, the first GPCR can be made to couple with the Gα to which the second GPCR couples. Such chimeric GPCRs are useful for adapting any GPCR, no matter with which Gα the first GPCR couples, to convenient high throughput assays.

The ability of a chimeric GPCR to bind a ligand and/or to trigger downstream signaling events can be assayed routinely. As such, a chimeric GPCR can be designed comprising any combination of sequences and can be tested for a desired function or activity without undue experimentation.

5.3.1 The Chimeric Intracellular Domain

Similar to the GPCR 8 from which chimeric GPCR 9 was designed, ICD 14' is composed of first intracellular loop 24', second intracellular loop 26', third intracellular loop 28' and C-terminal strand 30'. In chimeric GPCRs of the invention, at least two strands of first GPCR 8 are replaced with corresponding strands of a second GPCR. For example, third intracellular loop 28 can be replaced with third intracellular loop 28' from a second GPCR and C-terminal strand 30 can be replaced with C-terminal strand 30' from a second GPCR. The remaining strands of ICD 14' can correspond to the corresponding strands of the first GPCR, corresponding strands of the second GPCR, strands of other GPCRs, or strands of other proteins or novel sequences.

Preferably, replacing the intracellular strand alters the function of the first GPCR. For instance, replacing at least two intracellular strands from a first GPCR that couples with a first Gα protein with the corresponding intracellular strands of a second GPCR that couples with a second Gα protein can cause the resulting chimeric GPCR to couple with the second Gα protein. The remaining strands of the chimeric ICD can be replaced with corresponding strands from the second GPCR, with corresponding strands from other GPCRs, with strands from other polypeptides or with novel strands.

Preferred second GPCRs for the chimeric strands of the chimeric ICD include those GPCRs that are useful for high-throughput screening. Such GPCRs include, but are not limited to, GPCRs that couple with Gαq proteins. For example, preferred second GPCRs of the invention include Edg 2, Edg 3, Edg 4 and Edg 7.

In certain embodiments of the invention, one entire strand of the first GPCR is replaced by the entire corresponding strand of the second GPCR. However, in other embodiments of the invention, the starting and ending points (i.e., the N- and C-termini) of the segment of the first GPCR which is replaced can vary by one or more amino acids from the starting and ending points of the strand itself. In other words, for the purposes of the invention, the boundary between a TMD helix and an ICD strand can vary by one or more amino acid residues from the definition given above. For instance, one or more residues of an adjacent TMD helix can be replaced. If any residues of a TMD helix are replaced, the replacement preferably should be designed so as not to disrupt the structure of the resulting chimera and/or so as not to disrupt the ligand binding properties of the resulting chimera. The ligand binding properties of the chimera can be assayed readily according to the methods discussed below. In addition, one or more residues of the ICD strand can remain in the chimera. Preferably, the variation between the strand itself and the replaced segment is no more than 0, 1 or 2 amino acids at either end. Most preferably, the entire ICD strand is replaced and no residues of adjacent TMD helices are replaced.

Similarly, the starting point and ending point of the segment from the second GPCR which is included in the chimeric GPCR can match exactly the starting point or ending point of a strand in the second GPCR. Alternatively, the starting point and ending point can vary independently by one or more amino acids. The variation in the starting or ending points should not be so great as to significantly reduce the structure or function of the resulting chimeric GPCR. Preferably, the variation between the strand itself and the replacing segment is no more than 0, 1 or 2 amino acids at either end. Most preferably, the entire strand is included in the chimeric GPCR.

Furthermore, the amino acid sequence of the replacing strand can match exactly the sequence of a strand in the second GPCR. Alternatively, the replacing strand can possess one or more mutations relative to the strand of the second GPCR. In certain embodiments the mutations are conservative mutations, in other embodiments the mutations are non-conservative. The strand can also include genetically non-encoded amino acids. Preferably, the mutations do not significantly change the structure or reduce the function of the chimeric GPCR.

5.3.2 The Extracellular Domain

ECD 10' corresponds to ECD 10 of first GPCR 8. The amino acid sequence of ECD 10' may correspond identically to the amino acid sequence of ECD 10 of integral membrane protein 8. Alternatively, it may include one or more mutations, which may be conservative or non-conservative or consist of insertions or deletions, as are well-known in the art. The non-conservative mutations can include encoded or genetically non-encoded amino acids. Preferably, such mutated ECDs 10' will retain significant biological activity. Alternatively, chimeric GPCRs of the invention including mutated ECDs 10' of unknown activity may be designed and synthesized as a convenient means of assessing the affect of such mutations on the activity of ECD 10', and by correlation upon the ECD 10 of integral membrane protein 2 to which functional domain 10' corresponds. Preferably, the amino acid sequence of ECD 10' will correspond identically to the sequence of ECD 10.

5.3.3 Transmembrane Domain

In certain embodiments, TMD 12' corresponds to TMD 12 of first GPCR 8. The amino acid sequence of TMD 12' may correspond identically to the amino acid sequence of TMD 12 of integral membrane protein 8. Alternatively, it may include one or more mutations, which may be conservative or non-conservative or consist of insertions or deletions, as are well-known in the art. Preferably, such mutated TMDs 12' will retain at least some biological activity. Alternatively, chimeric GPCRs of the invention including mutated TMDs 12' of unknown activity may be designed and synthesized as a convenient means of assessing the effect of such mutations on the activity of TMD 12', and by correlation upon the TMD 12 of integral membrane protein 2 to which functional domain 10' corresponds. Preferably, the amino acid sequence of TMD 12' will correspond identically to the sequence of TMD 12.

In certain other embodiments, TMD 12' corresponds to the TMD of the second GPCR. Typically, all seven strands of TMD 12' correspond to the corresponding strands of the second GPCR. The amino acid sequence of TMD 12' may correspond identically to the amino acid sequence of the TMD of the second GPCR. Alternatively, it may include one or more mutations, which may be conservative or non-conservative or consist of insertions or deletions, as are well-known in the art. Preferably, such mutated TMDs 12' will retain at least some biological activity. Preferably, the amino acid sequence of TMD 12' will correspond identically to the sequence of the TMD of the second GPCR.

5.4 Spacers or Linkers

The chimeric intracellular strands and the appropriate transmembrane strand(s) can be linked together either directly or via an optional spacer or linker. The spacers or linkers of a chimeric GPCR can be any moieties known to those of skill in the art to be capable of linking one moiety to a second moiety. The spacer or linker may be rigid, semi-rigid or flexible, hydrophilic or hydrophobic, long or short, etc. A plethora of spacers or linkers suitable for linking strands or domains are known in the art. The actual choice of spacer or linker will depend upon, among other things, the nature of the chimeric GPCR, the length vs. rigidity of the spacer, etc., and will be apparent to those of skill in the art. Preferred spacers or linkers are peptides or polypeptides that do not interfere with the function of the chimeric GPCR. The function of the chimeric GPCR can be assayed readily according to the methods described below.

5.5 Chimeric Edg Receptors

In certain embodiments, the present invention provides chimeric Edg receptors. Edg receptors are encoded by endothelial differentiation genes and bind the lipid ligand lysophosphatidic acid or sphingosine-1-phosphate. Edg receptors have been implicated in ovarian cancer, prostate cancer, breast cancer, cardiovascular diseases and central nervous system disorders such as multiple sclerosis. A chimeric Edg receptor can be designed from a known Edg receptor including Edg 1, Edg 2, Edg 3, Edg 4, Edg 5, Edg 6, Edg 7 Edg 8 or any Edg receptor yet to be discovered. Preferred Edg receptors include, but are not limited to, human and rat Edg receptors.

To design a chimeric Edg receptor from a first Edg receptor, at least one ICD strand of the first Edg receptor is replaced with a corresponding strand from a second GPCR according to the description above. The corresponding strand is selected from a GPCR that couples with a Gα protein that triggers a signal that is compatible with a high-throughput screen. Such GPCRs include GPCRs that couple with a Gαq protein. In preferred embodiments, the corresponding strand is selected from a second Edg receptor.

In the ICD of a chimeric Edg receptor, any of the strands can be replaced with a corresponding strand of a second Edg receptor. In certain embodiments, more than one strand is replaced. In fact, three or even all four of the ICD strands can be replaced with corresponding strands from a second Edg receptor. In preferred embodiments, both the second intracellular loop and the third intracellular loop of the first Edg receptor are replaced with corresponding strands of the second Edg receptor. In further embodiments, the second intracellular loop, the third intracellular loop and the carboxy terminal strand of the first Edg receptor are replaced with corresponding strands of the second Edg receptor.

Referring to FIG. 1A and FIG. 1B, any of the ICD strands of first Edg receptor 8 (including first intracellular loop 24, second intracellular loop 26, third intracellular loop 28 and carboxy terminal strand 30) can be replaced with a corresponding strand from a second GPCR or from a second Edg receptor. In preferred embodiments more than one ICD strand of the first GPCR is replaced with a corresponding strand from a second GPCR or a second Edg receptor. For instance, in specific embodiments first intracellular loop 24, second intracellular loop 26, third intracellular loop 28 and carboxy terminal strand 30 of a first Edg receptor can all be replaced with corresponding strands of a second Edg receptor to generate a robust chimeric Edg receptor.

Particularly useful chimeric Edg receptors include those in which the first Edg receptor couples with a first Gα protein and the second Edg receptor couples with a second Gα protein. Those Edg receptors which couple with the Gαq protein and mobilize intracellular calcium include Edg 2, Edg 3, Edg 4 and Edg 7. The remaining Edg receptors (Edg 1, Edg 5, Edg 6 and Edg 8) do not couple with the Gαq protein and cannot mobilize intracellular calcium. Thus, preferred chimeric Edg receptors are designed from Edg 1, Edg 5, Edg 6 or Edg 8 and comprise a chimeric ICD having at least one strand from the ICD of Edg 2, Edg 3, Edg 4 or Edg 7. Such chimeric Edg receptors can be used in convenient high throughput assays to identify compounds that bind or modulate the activity of Edg 1, Edg 5, Edg 6 or Edg 8.

As discussed for chimeric GPCRs above, the ECD and/or TMD of a chimeric Edg receptor can correspond identically to the ECD and/or TMD of the first Edg receptor. Alternatively, each domain can have one or more mutations from the corresponding domain of the first Edg receptor. The mutations can be conservative or non-conservative.

Preferred chimeric Edg receptors retain the ligand binding properties of the first Edg receptor. Residues known to confer ligand binding specificity to the first Edg receptor should either not be altered in the chimeric GPCR or altered only conservatively. For instance, the Edg 1 residues $Arg^{120}$, $Arg^{292}$, and $Glu^{121}$ might be significant for substrate binding specificity (see Parrill et al., 2000, *J. Biol. Chem.* 275: 39379–39384). The activity and ligand binding specificity of chimeric Edg receptors can be determined by methods known to those of skill in the art as discussed below.

Non-limiting examples of native Edg receptors are presented in Table 2. In Table 2, italicized sequences indicate ICD strands (e.g. strand 24, 26, 28 or 30 of an Edg receptor), underlined sequences indicate TMD strands (e.g. strand 31, 33, 35, 37, 39, 41 or 43 of an Edg receptor), and plain text sequences indicate ECD strands (e.g., strand 16, 18, 20 or 22 of an Edg receptor).

TABLE 2

Amino Acid Sequences of Edg Receptors

| | | |
|---|---|---|
| Human Edg 1 Genbank Accession No. AF233365 | MGPTSVPLVKAHRSSVSDYVNYDIIVRHYNYTGKLNISADKENSI KLTSVVFILICCFIILENIFVLLTI*WKTKKFHR*PMYYFIGNLALS DLLAGVAYTANLLLSGATTYKLTPAQWFLRE*GSMFVALSASVFSL* *LAIAIERYITMLKMKLHNGSNNFR*LFLLISACWVISLILGGLPIM GWNCISALSSCSTVLPLYHKHYILFCTTVFTLLLLSIVILYCRIY *SLVRTRSRRLTFRKNISKASRSSEKSLALLK*TVIIVLSVFIACWA PLFILLLLDVGCKVKTCDILFR*AEYFLVLAVLNSGTNPIIYTLTN* *KEMRRAFIRIMSCCKCPSGDSAGKFKRPIIAGMEFSRSKSDNSSH* *PQKDEGDNPETIMSSGNVNSSS* | (SEQ ID NO:1) |
| Human Edg2 Genbank Accession No. U78192 | MAAISTSIPVISQPQFTAMNEPQCFYNESIAFFYNRSGKHLATEW NTVSKLVMGLGITVCIFIMLANLLVMVAI*YVNRRFHF*PIYYLMAN LAAADFFAGLAYFYLMFNTGPNTRRLTVSTWLLRQGLIDTSLTAS VANLLAIAI*ERHITVFRMQLHTRMSNRR*VVVVIVVIWTMAIVMGA IPSVGWNCICDIENCSNMAPLYSDSYLVFWAIFNLVTFVVMVVLY AHIFGYVRQRTMRMSRHSSGPRRNRDTMMSLLKTVVIVLGAFIIC | (SEQ ID NO:30) |

TABLE 2-continued

Amino Acid Sequences of Edg Receptors

| | | |
|---|---|---|
| | WTPGLVLLLLDVCCPQCDVLAYEKFFLLLAEFNSAMNPIIYSYRD | |
| | KEMSATFRQILCCQRSENPTGPTEGSDRSASSLNHTILAGVHSND | |
| | HSVV | |
| Human Edg 3 Genbank Accession No. X83864 | MATALPPRLQPVRGNETLREHYQYVGKLAGRLKEASEGSTLTTVL FLVICSFIVLENLMVLIAIWKNNKFHNRMYFFIGNLALCDLLAGI AYKVNILMSGKKTFSLSPTVWFLREGSMFVALGASTCSLLAIAIE RHLTMIKMRPYDANKRHRVFLLIGMCWLIAFTLGALPILGWNCLH NLPDCSTILPLYSKKYIAFCISIFTAILVTIVILYARIYFLVKSS SRKVANHNNSERSMALLRTVVIVVSVFIACWSPLFILFLIDVACR VQACPILFKAQWFIVLAVLNSAMNPVIYTLASKEMRRAFFRLVCN CLVRGRGARASPIQPALDPSRSKSSSSNNSSHSPKVKEDLPHTDP SSCIMDKNAALQNGIFCN | (SEQ ID NO:2) |
| Human Edg4 Genbank Accession No. AF233092 | MVIMGQCYYNETIGFFYNNSGKELSSHWRPKDVVVVALGLTVSVL VLLTNLLVIAAIASNRRFHQPIYYLLGNLAAADLFAGVAYLFLMF HTGPRTARLSLEGWFLRQGLLDTSLTASVATLLAIAVERHRSVMA VQLHSRLPRGRVVMLIVGVWVAALGLGLLPAHSWHCLCALDRCSR MAPLLSRSYLAVWALSSLLVFLLMVAVYTRIFFYVRRRVQRMAEH VSCHPRYRETTLSLVKTVVIILGAFVVCWTPGQVVLLLDGLGCES CNVLAVEKYFLLLAEANSLVNAAVYSCRDAEMRRTFRRLLCCACL RQSTRESVHYTSSAQGGASTRIMLPENGHPLMDSTL | (SEQ ID NO:31) |
| Human Edg 4 mt Genbank Accession No. AF011466 | MVIMGQCYYNETIGFFYNNSGKELSSHWRPKDVVVVALGLTVSVL VLLTNLLVIAAIASNRRFHQPIYYLLGNLAAADLFAGVAYLFLMF HTGPRTARLSLEGWFLRQGLLDTSLTASVATLLAIAVERHRSVMA VQLHSRLPRGRVVMLIVGVWVAALGLGLLPAHSWHCLCALDRCSR MAPLLSRSYLAVWALSSLLVFLLMVAVYTRIFFYVRRRVQRMAEH VSCHPRYRETTLSLVKTVVIILGAFVVCWTPGQVVLLLDGLGCES CNVLAVEKYFLLLAEANSLVNAAVYSCRDAEMRRTFRRLLCCACL RQSTRESVHYTSSAQGGASTRIMLPENGHPLMTPPFSYLELQRYA ASNKSTAPDDLWVLLAQPNQQD | (SEQ ID NO:32) |
| Human Edg 5 Genbank Accession No. AF034780 | MGSLYSEYLNPNKVQEHYNYTKETLETQETTSRQVASAFIVILCC AIVVENLLVLIAVARNSKFHSAMYLFLGNLAASDLLAGVAFVANT LLSGSVTLRLTPVQWFAREGSASITLSASVFSLLAIAIERHVAIA KVKLYGSDKSCRMLLLIGASWLISLVLGGLPILGWNCLGHLEACS TVLPLYAKHYVLCVVTIFSIILLAIVALYVRIYCVVRSSHADMAA PQTLALLKTVTIVLGVFIVCWLPAFSILLLDYACPVHSCPILYKA HYFFAVSTLNSLLNPVIYTWRSRDLRREVLRPLQCWRPGVGVQGR RRVGTPGHHLLPLRSSSSLERGMHMPTSPTFLEGNTVV | (SEQ ID NO:33) |
| Human Edg6 Genbank Accession No. | MNATGTPVAPESCQQLAAGGHSRLIVLHYNHSGRLAGRGGPEDGG LGALRGLSVAASCLVVLENLLVLAAITSHMRSRRWVYYCLVNITL SDLLTGAAYLANVLLSGARTFRLAPAQWFLREGLLFTALAASTFS | (SEQ ID NO:34) |

TABLE 2-continued

Amino Acid Sequences of Edg Receptors

| | |
|---|---|
| AJ000479 | LLFTAGERFATMVRPVAESGATKTSRVYGFIGLCWLLAALLGMLP |
| | LLGWNCLCAFDRCSSLLPLYSKRYILFCLVIFAGVLATIMGLYGA |
| | IFRLVQASGQKAPRPAARRKARRLLKTVMLILLAFLVCWGPLFGL |
| | LLADVFGSNLWAQEYLRGMDWILALAVLNSAVNPIIYSFRSREVC |
| | RAVLSFLCCGCLRLGMRGPGDCLARAVEAHSGASTTDSSLRPRDS |
| | FRGSRSLSFRMREPLSSISSVRSI |
| Human Edg7 Genbank Accession No. AF127138 | MNECHYDKHMDFFYNRSNTDTVDDWTGTKLVIVLCVGTFFCLFIF (SEQ ID NO:35) FSNSLVIAAVIKNRKFHFPFYYLLANLAAADFFAGIAYVFLMFNT GPVSKTLTVNRWFLRQGLLDSSLTASLTNLLVIAVERHMSIMRMR VHSNLTKKRVTLLILLVWAIAIFMGAVPTLGWNCLCNISACSSLA PIYSRSYLVFWTVSNLMAFLIMVVVYLRIYVYVKRKTNVLSPHTS GSISRRRTPMKLMKTVMTVLGAFVVCWTPGLVVLLLDGLNCRQCG VQHVKRWFLLLALLNSVVNPIIYSYKDEDMYGTMKKMICCFSQEN PERRPSRIPSTVLSRSDTGSQYIEDSISQGAVCNKSTS |
| Human Edg 8 Genbank Accession No. AF317676 | MESGLLRPAPVSEVIVLHYNYTGKLRGARYQPGAGLRADAVVCLA (SEQ ID NO:36) VCAFIVLENLAVLLVLGRHPRFHAPMFLLLGSLTLSDLLAGAAYA ANILLSGPLTLKLSPALWFAREGGVFVALTASVLSLLAIALERSL TMARRGPAPVSSRGRTLAMAAAAWGVSLLLGLLPALGWNCLGRLD ACSTVLPLYAKAYVLFCVLAFVGILAAICALYARIYCQVRANARR LPARPGTAGTTSTRARRKPRSLALLRTLSVVLLAFVACWGPLFLL LLLDVACPARTCPVLLQADPFLGLAMANSLLNPIIYTLTNRDLRH ALLRLVCCGRHSCGRDPSGSQQSASAAEASGGLRRCLPPGLDGSF SGSERSSPQRDGLDTSGSTGSPGAPTAARTLVSEPAAD |

Examples of chimeric Edg receptors of the invention are presented in Table 3. The chimeric Edg receptors listed in Table 3 are described in detail in the working examples presented below. In Table 3, italicized sequences indicate native ICD strands (e.g. native strand 24, 26, 28 or 30 of the Edg receptor). Bold sequences in the chimeric Edg receptors of Table 3 indicate strands from a second GPCR that have replaced the native strand of the first receptor at that position in the polypeptide sequence.

TABLE 3

Amino Acid Sequences of Chimeric Edg Receptors

| | | |
|---|---|---|
| Edg1/3(ct) | MGPTSVPLVKAHRSSVSDYVNYDIIVRHYNYTGKLNISADKENSI KLTSVVFILICCFIILENIFVLLTI*WKTKKFHR*PMYYFIGNLALS DLLAGVAYTANLLLSGATTYKLTPAQWFLREGSMFVALSASVFSL LAIA*IERYITMLKMKLHNGSNN*FRLFLLISACWVISLILGGLPIM GWNCISALSSCSTVLPLYHKHYILFCTTVFTLLLLSIVILYCRIY SLVR*TRSRRLTFRKNISKASRSSEKSLALLKTVI*IVLSVFIACWA PLFILLLLDVGCKVKTCDILFRAEYFLVLAVLNSGTNPIIYTLTS KEMRRAFFRLVCNCLVRGRGARASPIQPALDPSRSKSSSSNNSSH SPKVKEDLPHTDPSSCIMDKNAALQNGIFCN | (SEQ ID NO:3) |

TABLE 3-continued

Amino Acid Sequences of Chimeric Edg Receptors

| | | |
|---|---|---|
| Edg1/3(i3ct) | MGPTSVPLVKAHRSSVSDYVNYDIIVRHYNYTGKLNISADKENSI<br>KLTSVVFILICCFIILENIFVLLTI*WKTKKFHRP*MYYFIGNLALS<br><br>DLLAGVAYTANLLLSGATTYKLTPAQWFLREGSMFVALSASVFSL<br><br>LA*IAIERYITMLKMKLHNGSNNF*RLFLLISACWVISLILGGLPIM<br><br>GWNCISALSSCSTVLPLYHKHYILFCTTVFTLLLLSIVILYCRIY<br><br>SLVRSSSRKVANHNNSERSMALLRTVIIVLSVFIACWAPLFILLL<br><br>LDVGCKVKTCDILFRAEYFLVLAVLNSGTNPIIYTLTSKEMRRAF<br><br>FRLVCNCLVRGRGARASPIQPALDPSRSKSSSSNNSSHSPKVKED<br><br>LPHTDPSSCIMDKNAALQNGIFCN | (SEQ ID NO:4) |
| Edg1/3(i2i3ct) | MGPTSVPLVKAHRSSVSDYVNYDIIVRHYNYTGKLNISADKENSI<br>KLTSVVFILICCFIILENIFVLLTI*WKTKKFHRP*MYYFIGNLALS<br><br>DLLAGVAYTANLLLSGATTYKLTPAQWFLREGSMFVALSASVFSL<br><br>LAIAI*ERHLTMIKMRPYDANKRHR*LFLLISACWVISLILGGLPIM<br><br>GWNCISALSSCSTVLPLYHKHYILFCTTVFTLLLLSIVILYCRIY<br><br>SLVRSSSRKVANHNNSERSMALLRTVIIVLSVFIACWAPLFILLL<br><br>LDVGCKVKTCDILFRAEYFLVLAVLNSGTNPIIYTLTSKEMRRAF<br><br>FRLVCNCLVRGRGARASPIQPALDPSRSKSSSSNNSSHSPKVKED<br><br>LPHTDPSSCIMDKNAALQNGIFCN | (SEQ ID NO:5) |
| Edg 5/3(i3ct) | MGSLYSEYLNPNKVQEHYNYTKETLETQETTSRQVASAFIVILCC<br>AIVVENLLVLIAV*ARNSKFHS*AMYLFLGNLAASDLLAGVAFVANT<br><br>LLSGSVTLRLTPVQWFAREGSASITLSASVFSLLAIAI*ERHVAIA*<br><br>*KVKLYGSDKSC*RMLLLIGASWLISLVLGGLPILGWNCLGHLEACS<br><br>TVLPLYAKHYVLCVVTIFSIILLAIVALYVRIYCVVKSSSRKVAN<br><br>HNNSERSMALLRTVTIVLGVFIVCWLPAFSILLLDYACPVHSCPI<br><br>LYKAHYFFAVSTLNSLLNPVIYTWASKEMRRAFFRLVCNCLVRGR<br><br>GARASPIQPALDPSRSKSSSSNNSSHSPKVKEDLPHTDPSSCIMD<br><br>KNAALQNGIFCN | (SEQ ID NO:37) |
| Edg 8/4(ct) | MESGLLRPAPVSEVIVLHYNYTGKLRGARYQPGAGLRADAVVCLA<br>VCAFIVLENLAVLLVL*GRHPRFH*APMFLLLGSLTLSDLLAGAAYA<br><br>ANILLSGPLTLKLSPALWFAREGGVFVALTASVLSLLAIAL*ERSL*<br><br>*TMARRGPAPVSSRGR*TLAMAAAAWGVSLLLGLLPALGWNCLGRLD<br><br>ACSTVLPLYAKAYVLFCVLAFVGILAAICAL*YARIYCQVR*AN*ARR*<br><br>*LPARPGTAGTTSTRARRKPRS*LALLRTLSVVLLAFVACWGPLFLL<br><br>LLLDVACPARTCPVLLQADPFLGLAMANSLLNPIIYTLRDAEMRR<br><br>TFRRLLCCACLRQSTRESVHYTSSAQGGASTRIMLPENGHPLMTP<br><br>PFSYLELQRYAASNKSTAPDDLWVLLAQPNQQD | (SEQ ID NO:38) |

5.6 Nucleic Acids and Cells for Expressing Chimeric GPCRs

In another aspect, the present invention provides nucleic acids that can be used for the expression of the chimeric GPCRs of the invention. In particular, the present invention provides nucleic acids that are capable of expressing any of the chimeric GPCRs discussed above. For example, one nucleic acid of the present invention is capable of expressing the chimeric GPCR Edg 1/3(i3ct), and another is capable of expressing the chimeric GPCR Edg1/3(i2i3ct) (SEQ ID NO:5). Further nucleic acids of the invention are capable of expressing chimeric GPCR Edg1/3(ct) (SEQ ID NO:3), chimeric GPCR Edg 5/3(i3ct) (SEQ ID NO:37) or Edg 8/4(ct) (SEQ ID NO: 38).

The nucleic acid can be an RNA or a DNA and may be double stranded or single stranded. Typically, the nucleic acids of the present invention comprise a double stranded DNA or a single stranded RNA sequence that encodes a chimeric GPCR operably linked to a regulatory sequence that is capable of directing or effecting the expression of the chimeric GPCR.

The regulatory sequence of the nucleic acid should be selected based upon the expression system. For instance, a particularly useful nucleic acid is a DNA expression vector that is capable of encoding a chimeric GPCR. As used herein, the term "vector" refers to a nucleic acid molecule capable of transporting another nucleic acid to which it has been linked. One type of vector is a "plasmid", which refers to a circular double stranded DNA loop into which additional DNA segments can be ligated. Another type of vector is a viral vector, wherein additional DNA segments can be ligated into the viral genome. Certain vectors are capable of autonomous replication in a host cell into which they are introduced (e.g., bacterial vectors having a bacterial origin of replication and episomal mammalian vectors). Other vectors (e.g., non-episomal mammalian vectors) are integrated into the genome of a host cell upon introduction into the host cell, and thereby are replicated along with the host genome. Moreover, certain vectors, expression vectors, are capable of directing the expression of genes to which they are operably linked. In general, expression vectors of utility in recombinant DNA techniques are often in the form of plasmids (vectors). However, the invention is intended to include such other forms of expression vectors, such as viral vectors (e.g., replication defective retroviruses, adenoviruses and adeno-associated viruses), which serve equivalent functions. A particularly convenient vector is a cassette vector which comprises expression cassettes, as previously described.

The recombinant expression vectors of the invention comprise a nucleic acid of the invention in a form suitable for expression of the nucleic acid in a host cell. This means that the recombinant expression vectors include one or more regulatory sequences, selected on the basis of the host cells to be used for expression, which is operably linked to the nucleic acid sequence to be expressed. Within a recombinant expression vector, "operably linked" is intended to mean that the nucleotide sequence of interest is linked to the regulatory sequence(s) in a manner which allows for expression of the nucleotide sequence (e.g., in an in vitro transcription/translation system or in a host cell when the vector is introduced into the host cell). The term "regulatory sequence" is intended to include promoters, enhancers and other expression control elements (e.g., polyadenylation signals). Such regulatory sequences are described, for example, in Goeddel, *Gene Expression Technology: Methods in Enzymology* 185, Academic Press, San Diego, Calif. (1990). Regulatory sequences include those which direct constitutive expression of a nucleotide sequence in many types of host cell and those which direct expression of the nucleotide sequence only in certain host cells (e.g., tissue-specific regulatory sequences). It will be appreciated by those skilled in the art that the design of the expression vector can depend on such factors as the choice of the host cell to be transformed, the level of expression of protein desired, etc. The expression vectors of the invention can be introduced into host cells to thereby produce proteins or peptides encoded by nucleic acids as described herein.

The recombinant expression vectors of the invention can be designed for expression of a chimeric GPCR of the invention in prokaryotic (e.g., *E. coli*) or eukaryotic cells (e.g., insect cells (using baculovirus expression vectors), yeast cells or mammalian cells). Suitable host cells are discussed further in Goeddel, supra. Alternatively, the recombinant expression vector can be transcribed and translated in vitro, for example using T7 promoter regulatory sequences and T7 polymerase.

Expression of proteins in prokaryotes is most often carried out in *E. coli* with vectors containing constitutive or inducible promoters directing the expression of chimeric GPCR. A chimeric GPCR can be expressed with a fusion vector or a non-fusion vector. Fusion vectors add a number of amino acids to a protein encoded therein, usually to the amino terminus of the recombinant protein. Such fusion vectors typically serve three purposes: 1) to increase expression of recombinant protein; 2) to aid in the purification of the recombinant protein by acting as a ligand in affinity purification; and 3) to direct the cellular location of the recombinant protein (e.g. with signal peptides for secretion). Often, in fusion expression vectors, a proteolytic cleavage site is introduced at the junction of the fusion moiety and the recombinant protein to enable separation of the recombinant protein from the fusion moiety subsequent to purification of the fusion protein. Such enzymes, and their cognate recognition sequences, include Factor Xa, thrombin and enterokinase. Typical fusion expression vectors include pGEX (Pharmacia Biotech Inc; Smith and Johnson, 1988, *Gene* 67:31–40), pMAL (New England Biolabs, Beverly, Mass.) and pRIT5 (Pharmacia, Piscataway, N.J.) which fuse glutathione S-transferase (GST), maltose E binding protein, or protein A, respectively, to the target recombinant protein.

Examples of suitable inducible non-fusion *E. coli* expression vectors include pTrc (Amann et al., 1988, *Gene* 69:301–315) and pET 11d (Studier et al., *Gene Expression Technology: Methods in Enzymology* 185, Academic Press, San Diego, Calif. (1990) 60–89). Target gene expression from the pTrc vector relies on host RNA polymerase transcription from a hybrid trp-lac fusion promoter. Target gene expression from the pET 11d vector relies on transcription from a T7 gn10-lac fusion promoter mediated by a coexpressed viral RNA polymerase (T7 gn1). This viral polymerase is supplied by host strains BL21(DE3) or HMS174 (DE3) from a resident λ prophage harboring a T7 gn1 gene under the transcriptional control of the lacUV 5 promoter.

One strategy to maximize recombinant protein expression in *E. coli* is to express the protein in a host bacteria with an impaired capacity to proteolytically cleave the recombinant protein (Gottesman, *Gene Expression Technology: Methods in Enzymology* 185, Academic Press, San Diego, Calif. (1990) 119–128). Another strategy is to alter the nucleic acid sequence of the nucleic acid to be inserted into an expression vector so that the individual codons for each amino acid are those preferentially utilized in *E. coli* (Wada et al., 1992, *Nucleic Acids Res.* 20:2111–2118). Such alteration of nucleic acid sequences of the invention can be carried out by standard DNA synthesis techniques.

In another embodiment, the expression vector is a eukaryotic expression vector. Examples of eukaryotic expression vectors include fusion vectors similar to the prokaryotic fusion vectors discussed above, such as vectors that include a signal peptide fusion to direct secretion of the recombinant protein.

For instance, the expression vector is a yeast expression vector. Examples of vectors for expression in yeast *S. cerivisae* include pYepSec1 (Baldari et al., 1987, *EMBO J.*

6:229–234), pMFa (Kurjan and Herskowitz, 1982, *Cell* 30:933–943), pJRY88 (Schultz et al., 1987, *Gene* 54:113–123), pYES2 (Invitrogen Corporation, San Diego, Calif.), and pPicZ (Invitrogen Corp, San Diego, Calif.).

Alternatively, the expression vector is a baculovirus expression vector. Baculovirus vectors available for expression of proteins in cultured insect cells (e.g., Sf 9 cells) include the pAc series (Smith et al., 1983, *Mol. Cell Biol.* 3:2156–2165) and the pVL series (Lucklow and Summers, 1989, *Virology* 170:31–39).

In yet another embodiment, a nucleic acid of the invention is expressed in mammalian cells using a mammalian expression vector. Examples of mammalian expression vectors include pCDM8 (Seed, 1987, *Nature* 329:840) and pMT2PC (Kaufman et al., 1987, *EMBO J.* 6:187–195). When used in mammalian cells, the expression vector's control functions are often provided by viral regulatory elements. For example, commonly used promoters are derived from polyoma, Adenovirus 2, cytomegalovirus and Simian Virus 40 (SV40). For other suitable expression systems for both prokaryotic and eukaryotic cells see chapters 16 and 17 of Sambrook et al., supra.

In another embodiment, the recombinant mammalian expression vector is capable of directing expression of the nucleic acid preferentially in a particular cell type (e.g., tissue-specific regulatory elements are used to express the nucleic acid). Tissue-specific regulatory elements are known in the art. Non-limiting examples of suitable tissue-specific promoters include the albumin promoter (liver-specific; Pinkert et al., 1987, *Genes Dev.* 1:268–277), lymphoid-specific promoters (Calame and Eaton, 1988, *Adv. Immunol.* 43:235–275), in particular promoters of T cell receptors (Winoto and Baltimore, 1989, *EMBO J.* 8:729–733) and immunoglobulins (Banerji et al., 1983), Cell 33:729–740; Queen and Baltimore, 1983), Cell 33:741–748), neuron-specific promoters (e.g., the neurofilament promoter; Byrne and Ruddle, 1989, *Proc. Natl. Acad. Sci. USA* 86:5473–5477), pancreas-specific promoters (Edlund et al., 1985, *Science* 230:912–916), and mammary gland-specific promoters (e.g., milk whey promoter; U.S. Pat. No. 4,873,316 and European Application Publication No. 264,166). Developmentally-regulated promoters are also encompassed, for example the mouse hox promoters (Kessel and Gruss, 1990, *Science* 249:374–379) and the beta-fetoprotein promoter (Campes and Tilghman, 1989, *Genes Dev.* 3:537–546).

Another aspect of the invention pertains to host cells into which a recombinant expression vector of the invention has been introduced. The terms "host cell" and "recombinant host cell" are used interchangeably herein. It is understood that such terms refer not only to the particular subject cell but to the progeny or potential progeny of such a cell. Because certain modifications may occur in succeeding generations due to either mutation or environmental influences, such progeny may not, in fact, be identical to the parent cell, but are still included within the scope of the term as used herein.

A host cell can be any prokaryotic (e.g., *E. coli*) or eukaryotic cell (e.g., insect cells, yeast or mammalian cells). Host cells intended to be part of the invention include ones that comprise a nucleic acid molecule of the invention that has been engineered to be present within the host cell (e.g., as part of a vector), and ones that comprise nucleic acid regulatory sequences that have been engineered to be present in the host cell such that a nucleic acid molecule of the invention is expressed within the host cell.

Vector DNA can be introduced into prokaryotic or eukaryotic cells via conventional transformation or transfection techniques. The prokaryotic or eukaryotic cells can be transformed or transfected either stably or transiently. As used herein, the terms "transformation" and "transfection" are intended to refer to a variety of art-recognized techniques for introducing foreign nucleic acid into a host cell, including calcium phosphate or calcium chloride co-precipitation, DEAE-dextran-mediated transfection, lipofection, electroporation, viral infection or microinjection. Suitable methods for transforming or transfecting host cells can be found in Sambrook, et al. (supra), and other laboratory manuals.

For stable transfection of mammalian cells, it is known that, depending upon the expression vector and transfection technique used, only a small fraction of cells may integrate the foreign DNA into their genome. In order to identify and select these integrants, a gene that encodes a selectable marker (e.g., for resistance to antibiotics) is generally introduced into the host cells along with the gene of interest. Preferred selectable markers include those which confer resistance to drugs, such as G418, hygromycin and methotrexate. Cells stably transfected with the introduced nucleic acid can be identified by drug selection (e.g., cells that have incorporated the selectable marker gene will survive, while the other cells die).

A host cell of the invention, such as a prokaryotic or eukaryotic host cell in culture, can be used to produce a polypeptide of the invention. Accordingly, the invention further provides methods for producing a chimeric GPCR of the invention using the host cells of the invention. In one embodiment, the method comprises culturing the host cell of invention (into which a recombinant expression vector encoding a polypeptide of the invention has been introduced) in a suitable medium such that the polypeptide is produced. In another embodiment, the method further comprises isolating the polypeptide from the medium or the host cell.

Particularly useful cell types for expressing and assaying the chimeras include, but are not limited to, HTC4 (rat hepatoma cells), RH7777 (rat hepatoma cells), HepG2 (human hepatoma cells), CHO (Chinese hamster ovary cells), HEK-293 (human embryonic kidney cells). Particularly useful vectors for expressing chimeric GPCRs include, but are not limited to pLXSN and pCMV.

DNA encoding a chimeric GPCR can be transfected into human or mammalian cells according to methods known to those of skill in the art. For example, DNA encoding a chimeric GPCR can be co-transfected with a standard packaging vector which provides an ecotropic envelope for viral replication, into a packaging cell line such as GP-293 (Clontech Labs., Palo Alto, Calif.). Cell line GP-293 has integrated in its genome gag and pol, genes necessary for viral packaging from vesicular stomatitis virus. Alternatively, DNA encoding a chimeric GPCR can be transfected into the EcoPack-293 cell line which has, in addition to gag and pol, the env gene to produce an ecotropic envelope. Both methods (i.e. co-transfection with a packaging vector or use of EcoPack-293) enable the production of an ecotropic envelope for viral packaging, and can thus advantageously be used to transfect rat and mouse cells. For use in human and other mammalian cells, AmphoPack-293 cell line (Clontech, Palo Alto, Calif.) can be used.

5.7 Methods of Producing Chimeric GPCRs

The chimeric GPCRs of the present invention can be produced by a variety of means. For example, chimeric GPCRs of the invention that are entirely of gene-encoded amino acids may be produced recombinantly using any of the nucleic acids and expression vectors described above. Alternatively, all of the chimeric GPCRs of the invention may be produced by synthetic or semi-synthetic means. Chimeric GPCRs comprising non-encoded amino acids, for example, can be produced by synthetic or semi-synthetic means.

For example, the polypeptide portions of a chimeric GPCR can be produced by recombinant techniques or by standard chemical synthesis techniques such as those described by Merrifield, 1997, *Meth. Enzymol.* 289:3–13 (see also Williams et al., 1997, *Chemical Approaches to the Synthesis of Peptides and Proteins*, CRC Press, Boca Raton; Atherton & Sheppard, 1989, *Solid Phase Peptide Synthesis*, Oxford University Press, New York). The polypeptide portions of the chimeric GPCR can then be linked together by standard synthetic techniques. For instance, peptide or polypeptide portions of the chimeric GPCR can be linked together by standard techniques for forming amide linkages. Other portions of the chimeric GPCR, such as non-peptide and non-polypeptide linking molecules, can be linked to the appropriate portions of the chimeric GPCR also by standard synthetic techniques. The appropriate techniques will depend on the reactive groups of the portions of the chimeric GPCR to be linked together, and will be readily apparent to those of skill in the art.

5.8 Uses

The chimeric GPCRs polypeptides of the invention can be used in virtually any assay or method in which the GPCRs from which they were designed are useful and in other methods. Such methods include calcium mobilization assays, binding assays, detection of cAMP formation, reporter gene techniques and other methods known to those of skill in the art. Owing to their altered downstream signaling functions, they find particular use, for example, in convenient high throughput assays.

The chimeric GPCRs of the invention can be used to identify a compound that selectively binds to and/or modulates the activity of the first GPCR, or domain thereof, from which the chimeric GPCR of the invention was designed. Compounds identified in this manner can be tested for an ability to modulate biological processes and/or disorders associated with the first GPCR. In general, such methods comprise contacting a test compound with a chimeric GPCR and assaying for the presence of the bound test compound or assaying for modulation of the activity of the chimeric GPCR. The chimeric GPCR can be, for example, expressed on the surface of a cell.

As used herein the term "selectively binds" refers to a compound (e.g., an antibody, a peptide, a lipid or a small organic molecule) that binds to a native polypeptide or to a chimeric polypeptide preferentially relative to other unrelated polypeptides. A compound selectively binds to the native polypeptide or a chimeric polypeptide of the invention if it has at least a 10%, preferably at least a 25%, at least a 50%, at least a 75%, at least a 90%, at least a 95%, or at least a 100% higher affinity and/or avidity for the native polypeptide or chimeric polypeptide than an unrelated polypeptide.

The assay for the presence of the bound test compound can be any assay known to those of skill in the art to be useful for assaying binding to the first GPCR or to the chimeric GPCR and/or any assay known to those of skill in the art to be useful for assaying activation of the first GPCR or of the chimeric GPCR. In particularly convenient embodiments of the invention, the presence of the test compound can be assayed by detecting the activity of a downstream effector of the chimeric GPCR such as phospholipase C (PLC) activity and/or mobilization of intracellular calcium. A compound that binds the chimeric GPCR can then be tested against the native first GPCR according to standard techniques.

The assay for the modulation of the activity of the chimeric GPCR can be any assay known to those of skill in the art to be useful for assaying the activity of the chimeric GPCR. Such an assay can be used to screen for agonists or antagonists of the first GPCR and/or agonists or antagonists of the chimeric GPCR. In particularly convenient embodiments of the invention, a chimeric GPCR is contacted with a test compound. Optionally, the chimeric GPCR can also be contacted with a ligand of the first GPCR and/or a ligand of the chimeric GPCR, for example, in assays for antagonists of the first GPCR and/or the chimeric GPCR. The ability of the test compound to modulate the activity of the chimeric GPCR can be assayed by detecting a change in the activity of a downstream effector of the chimeric GPCR such as phospholipase C (PLC) activity and/or mobilization of intracellular calcium. A compound that modulates the activity of the chimeric GPCR can then be tested against the native first GPCR according to standard techniques.

Specific assays for GPCR or chimeric GPCR activity are known to those of skill in the art. For example, cells expressing a GPCR or a chimeric GPCR can be contacted with a membrane-permeant calcium sensitive dye such as Fluo-4 AM or a proprietary calcium dye loading kit (e.g., FLIPR Calcium Assay kit, Molecular Devices, Sunnyvale, Calif.). Intracellular calcium is capable of binding to the dye and emitting fluorescent radiation when illuminated at the appropriate wavelength. The cells can thus be illuminated an appropriate wavelength for the dye and any emitting light can be captured by a cooled CCD camera. Changes in fluorescence indicate changes in intracellular calcium resulting from the activation of a $G\alpha q$—coupled GPCR. Such changes can be measured advantageously in whole cells in "real-time" (Berridge et al., Nature Reviews 2000 1:11–21).

Other methods of measuring intracellular calcium are known to those of skill in the art. For instance, a commonly used technique is the expression of receptors of interest in *Xenopus laevis* oocytes followed by measurement of calcium activated chloride currents (see Weber, 1999, *Biochim Biophys Acta* 1421:213–233). In addition, several calcium sensitive dyes are available for the measurement of intracellular calcium. Such dyes can be membrane permeant or not membrane permeant. Examples of useful membrane permeant dyes include acetoxymethyl ester forms of dyes that can be cleaved by intracellular esterases to form a free acid, which is no longer membrane permeant and remains trapped inside a cell. Dyes that are not membrane permeant can be introduced into the cell by microinjection, chemical permeabilization, scrape loading and similar techniques (Haughland, 1993, in "Fluorescent and Luminescent Probes for Biological Activity" ed. Mason, W. T. pp 34–43; Academic Press, London; Haughland, 1996, in "Handbook of Fluorescent Probes and Research Chemicals", sixth edition, Molecular Probes, Eugene, Oreg.).

Furthermore, other assays can be used to detect receptor-mediated G-protein activation (see, e.g., "Regulation of G Protein-Coupled Receptor Function and Expression" ed. Benovic, J. L. pp 119–132., 2000, Wiley-Liss, New York). Such assays include receptor-stimulated GTP Binding to $G\alpha$ subunits. Since activation of GPCR results in GDP-GTP exchange in the $G\alpha$ subunit, this exchange can be quantified and used as a direct measurement of receptor-G protein interaction. This typically involves the use of radiolabeled guanine nucleotide ($^{35}$S-GTPγS or $α^{32}$P-GTP) incubated with the receptor (either in cell free membrane preparations or aritifical lipid membranes). The amount of $^{35}$S-GTPγS incorporated can be used as a measure of the extent of G protein activation.

Other useful assays include changes in intrinsic tryptophan fluorescence of Gα subunits. The intrinsic fluorescence of tryptophan residues undergoes an enhancement during GDP-GTP exchange. Virtually all the Gα subunits have a conserved Trp residue in a domain that undergoes significant conformational change during activation of the Gα subunit.

Another assay for receptor mediated G-protein activation is measurement of the hydrolysis of GTP by Gα. The final outcome of Gα activation is hydrolysis of bound GTP to GDP by intrinsic GTPase activity. Using $γ^{32}$P-GTP, the release of $^{32}$P$_i$ upon GTP-GDP exchange can be used as an indication of G-protein activation.

Those of skill in the art will recognize appropriate control experiments for the assays for binding to a chimeric GPCR or modulation of the activity of a chimeric GPCR. For instance, the test compound can be assayed against a second, native or chimeric GPCR with different ligand binding properties under similar conditions.

The invention having been described, the following examples are intended to illustrate, and not limit, this invention.

6. EXAMPLES

6.1 Preparation of Vector for Expression of Chimeric GPCR Edg 1/3(ct)

This example demonstrates the construction of a vector for the expression of a chimeric Edg receptor, Edg 1/3(ct), which is designed from Edg 1 and includes the carboxy terminal ("ct") strand from Edg 3.

cDNA encoding the wild type Edg 1 receptor and wild-type Edg 3 receptor were obtained from Dr. Edward Goetzl (UCSF) and subdloned into the pLXSN vector (Clontech Labs, Palo Alto, Calif.).

A vector for expressing Edg 1/3(ct) was produced by PCR-based, splice-overlap mutagenesis in which the carboxy terminal strand of Edg 1 was replaced with the carboxy terminal stand of Edg3.

In particular, a first DNA encoding all of Edg 1 except the carboxy terminal strand (amino acid residues 1–314 of Edg 1) was produced by PCR with primers SEQ ID NO:6 and SEQ ID NO:9 using the Edg 1 cDNA as a template. Primer sequences used to construct chimeric Edg 1 polypeptides are listed in Table 4, below. A second DNA encoding the carboxy terminal strand of Edg 3 (Edg 3 amino acid residues 302–378) was produced by PCR with primers SEQ ID NO:7 and SEQ ID NO:8 using the Edg 3 cDNA as a template. PCR reactions comprised 1 ng/μL template, 40 ng/μL each primer, 0.2 mM dNTPs, 0.02 U/μL VENT™ polymerase in 1× Thermopol™ buffer (Mullis, K. et al. 1996, Cold Spring Harbor Symposia on Quantitative Biology 51:263). The PCR reactions comprised 35 cycles at an annealing temperature of 55° C. for 45 seconds.

DNA encoding the full length Edg 1/3(ct) chimera was produced in a secondary PCR reaction with primers SEQ ID NO:6 and SEQ ID NO:7 and using 10 μl each of the first and second DNA generated from the primary 50 μl PCR reaction as the template. The first and second DNA had overlapping complementary ends. PCR reactions comprised 40 ng/μl of each primer, 0.2 mM dNTPs, 0.02 U/μl VENT™ polymerase in 1× Thermopol™ buffer (Carruthers et al. 1994 JBC 269:29321; adapted from Short Protocols in Molecular Biology. 3$^{rd}$ edition 1995 John Wiley and Sons, Inc. New York, N.Y.). The PCR reactions comprised 35 cycles at an annealing temperature of 55° C. for 45 seconds.

The accuracy of each PCR step was verified by dideoxy sequencing.

6.2 Preparation of Vector for Expression of Chimeric GPCR Edg 1/3(i3ct)

This example demonstrates the construction of a vector for the expression of a chimeric Edg receptor, Edg 1/3(i3ct), which is designed from Edg 1 and includes two intracellular strands (the third intracellular loop ("i3") and the carboxy terminal strand) from Edg 3.

A vector for expressing Edg 1/3(i3ct) was produced by PCR-based, splice-overlap mutagenesis in which the third intracellular strand of Edg 1/3(ct) was replaced with the third intracellular strand of Edg3. DNA encoding the chimeric Edg 1/3(ct) receptor was prepared as described in Example 6.1, above, and DNA encoding Edg 3 was obtained as described in Example 6.1.

A first DNA encoding the portion of Edg 1 from the amino terminus through amino acid 229 was produced by PCR with primers SEQ ID NO:6 and SEQ ID NO:15 using the Edg 1/3(ct) DNA as a template. A second DNA encoding the third intracellular loop of Edg 3 (Edg 3 residues 224–243) was produced by PCR with primers SEQ ID NO:14 and SEQ ID NO:17 using the Edg 3 cDNA as a template. A third DNA encoding the portion of Edg 1/3(ct) from amino acid 257 through the carboxy terminus was produced by PCR with primers SEQ ID NO:16 and SEQ ID NO:7 using the Edg 1/3(ct) DNA as a template. The first and second DNA had overlapping complementary ends, and the second and third DNA had overlapping complementary ends. PCR reactions comprised about 1 ng/μL template, 40 ng/μL each primer, 0.2 mM dNTPs, 0.02 U/μL VENT™ polymerase in 1× Thermopol™ buffer (Mullis, K. et al. 1996. Cold Spring Harbor Symposia on Quantitative Biology 51:263). The PCR reactions comprised 35 cycles at an annealing temperature of 55° C. for 45 seconds.

A fourth DNA encoding a portion of the Edg 1/3(i3ct) chimera was produced in a secondary PCR reaction with primers SEQ ID NO: 6 and SEQ ID NO: 17 and using 10 μl each of the first and second DNA generated from the primary 50 μl PCR reaction as the template. DNA encoding the full length Edg 1/3(i3ct) chimera was then produced in a tertiary PCR reaction with primers SEQ ID NO: 6 and SEQ ID NO: 7 and using 10 μl each of the third and fourth DNA generated from the primary 50 μl PCR reaction as the template. The first and second DNA, and the third and fourth DNA had overlapping complementary ends. PCR reactions comprised 40 ng/μl of each primer, 0.2 mM dNTPs, 0.02 U/μl VENT™ polymerase in 1× Thermopol™ buffer buffer (Carruthers et al. 1994 JBC 269:29321; adapted from Short Protocols in Molecular Biology. 3$^{rd}$ edition 1995 John Wiley and Sons, Inc. New York, N.Y.). The PCR reactions comprised 35 cycles at an annealing temperature of 55° C. for 45 seconds.

The accuracy of each PCR step was verified by dideoxy sequencing.

6.3 Preparation of Vector for Expression of Chimeric GPCR Edg 1/3(i2i3ct)

This example demonstrates the construction of a vector for the expression of a chimeric Edg receptor, Edg 1/3 (i2i3ct), which is designed from Edg 1 and includes three ICD strands (the second intracellular loop ("i2"), the third intracellular loop and the carboxy terminal strand) from Edg 3.

A vector for expressing Edg 1/3(i2i3ct) was produced by PCR-based, splice-overlap mutagenesis in which the second intracellular strand of Edg 1/3(i3ct) was replaced with the second intracellular strand of Edg3. DNA encoding the chimeric Edg 1/3(i3ct) receptor was prepared as described in Example 6.2, above, and DNA encoding Edg 3 was obtained as described in Example 6.1, above.

A first DNA encoding the portion of Edg 1 from the amino terminus through amino acid 140 was produced by PCR with primers SEQ ID NO:6 and SEQ ID NO:11 using the Edg 1/3(i3ct) DNA as a template. A second DNA encoding the second intracellular loop of Edg 3 (Edg 3 residues 135–153) was produced by PCR with primers SEQ ID NO:10 and SEQ ID NO:13 using the Edg 3 cDNA as a template. A third DNA encoding the portion of Edg 1/3(i3ct) from amino acid 160 through the carboxy terminus was produced by PCR with primers SEQ ID NO:12 and SEQ ID NO:7 using the Edg 1/3(i3ct) DNA as a template. PCR reactions comprised about 1 ng/µL template, 40 ng/µL each primer, 0.2 mM dNTPs, 0.02 U/µL VENT™ polymerase in 1× Thermopol™ buffer (Mullis, K. et al. 1996. Cold Spring Harbor Symposia on Quantitative Biology 51:263). The PCR reactions typically comprised 35 cycles at an annealing temperature of 55° C. for 45 seconds.

A fourth DNA encoding a portion of the Edg 1/3(i3ct) chimera was produced in a secondary PCR reaction with primers SEQ ID NO:6 and SEQ ID NO: 13 and using 10 µl each of the first and second DNA generated from the primary 50 µl PCR reaction as the template. DNA encoding the full length Edg 1/3(i2i3ct) chimera was then produced in a tertiary PCR reaction with primers SEQ ID NO: 6 and SEQ ID NO: 7 and using 10 µl each of the third and fourth DNA generated from the primary 50 µl PCR reaction as the template. The first and second DNA, and the third and fourth DNA had overlapping complementary ends. PCR reactions comprised 40 ng/µl of each primer, 0.2 mM dNTPs, 0.02 U/µl VENT™ polymerase in 1× Thermopol™ buffer buffer (Carruthers et al. 1994 JBC 269:29321; adapted from Short Protocols in Molecular Biology. 3$^{rd}$ edition 1995 John Wiley and Sons, Inc. New York, N.Y.). The PCR reactions comprised 35 cycles at an annealing temperature of 55° C. for 45 seconds.

The accuracy of each PCR step was verified by dideoxy sequencing.

TABLE 4

PCR Primers for Generating Chimeric Edg 1 Receptors

| Primer | Direction | Position | Sequence 5'-3' |
|---|---|---|---|
| Edg-1 (SEQ ID NO:6) |  | 1 | CCC/GCG/GTT/AAC/ATG/GGG/CCC/ACC/AGC/GTC |
| Edg-3 (SEQ ID NO:7) | rev | 1137 | CGC/GGA/TCC/TCA/GTT/GCA/GAA/GAT/CCC |
| E1/3 CTD (SEQ ID NO:8) |  | 942 | CAT/TTA/CAC/TCT/GAC/CAG/CAA/GGA/GAT/GCG/GCG/G |
| E1/3 CTD (SEQ ID NO:9) | rev | 942 | CCG/CAT/CTC/CTT/GCT/GGT/CAG/AGT/GTA/AAT/GAT/G |
| E1/3 i2 (SEQ ID NO:10) |  | 402 | GTC/TCC/TCG/CCA/TCG/CCA/TCG/AGC/GGC/ACT/TGA/C |
| E1/3 i2 (SEQ ID NO:11) | rev | 402 | GTC/AAG/TGC/CGC/TCG/ATG/GCG/ATG/GCG/AGG/AGA |
| E1/3 i2 (SEQ ID NO:12) |  | 441 | CGC/CAA/CAA/GAG/GCA/CCG/CCT/CTT/CCT/GCT/AAT/C |
| E1/3 i2 (SEQ ID NO:13) | rev | 441 | GAT/TAG/CAG/GAA/GAG/GCG/GTG/CCT/CTT/GTT/GGC/G |
| E1/3 i3 (SEQ ID NO:14) |  | 684 | CTA/CTC/CTT/GGT/CAG/GTC/CAG/CAG/CCG/TAA/GGT/G |
| E1/3 i3 (SEQ ID NO:15) | rev | 684 | CAC/CTT/ACG/GCT/GCT/GGA/CCT/GAC/CAA/GGA/GTA/G |
| E1/3 i3 (SEQ ID NO:16) |  | 723 | CAC/TGC/TGC/GGA/CCG/TGA/TTA/TCG/TCC/TGA/GCG/TC |
| E1/3 i3 (SEQ ID NO:17) | rev | 723 | GAC/GCT/CAG/GAC/GAT/AAT/CAC/GGT/CCG/CAG/CAG/TG |

6.4 Preparation of Vector for Expression of Chimeric GPCR Edg 5/3(ct)

This example demonstrates the construction of a vector for the expression of a chimeric Edg receptor, Edg 5/3(ct), which is designed from Edg 5 and includes the carboxy terminal strand from Edg 3.

cDNA encoding the wild type Edg 5 receptor and wild-type Edg 3 receptor were obtained from Dr. Edward Goetzl (UCSF) and subcloned into the pLXSN vector (Clontech Labs, Palo Alto, Calif.).

A vector for expressing Edg 5/3(ct) was produced by PCR-based, splice-overlap mutagenesis in which the carboxy terminal strand of Edg 5 was replaced with the carboxy terminal domain of Edg3.

In particular, a first DNA encoding all of Edg 5 except the carboxy terminal strand (Edg 5 residues 1–290) was produced by PCR with primers SEQ ID NO:18 and SEQ ID NO:21 using the Edg 5 cDNA as a template. Primer sequences used in construction of chimeric Edg 5 receptor are listed in Table 5, below. A second DNA encoding the carboxy terminal strand of Edg 3 (Edg 3 residue 301–378) was produced by PCR with primers SEQ ID NO:20 and SEQ ID NO:19 using the Edg 3 cDNA as a template. PCR reactions comprised about 1 ng/µL template, 40 ng/µL each primer, 0.2 mM dNTPs, 0.02 U/µL VENT™ polymerase in 1× Thermopol™ buffer (Mullis, K. et al. 1996. Cold Spring Harbor Symposia on Quantitative Biology 51:263). The PCR reactions comprised 35 cycles at an annealing temperature of 55° C. for 45 seconds.

DNA encoding the full length Edg 5/3(ct) chimera was produced in a secondary PCR reaction with primers SEQ ID NO:18 and SEQ ID NO:19 and using 10 µl each of the first and second DNA generated from the primary 50 µl PCR reaction as the template. The first and second DNA had overlapping complementary ends. PCR reactions comprised 40 ng/µl of each primer, 0.2 mM dNTPs, 0.02 U/µl VENT™ polymerase in 1×Thermopol™ buffer (Carruthers et al. 1994 JBC 269:29321; adapted from Short Protocols in Molecular Biology. 3$^{rd}$ edition 1995 John Wiley and Sons, Inc. New York, N.Y.). The PCR reactions comprised 35 cycles at an annealing temperature of 55° C. for 45 seconds.

The accuracy of each PCR step was verified by dideoxy sequencing.

6.5 Preparation of Vector for Expression of Chimeric GPCR Edg 5/3(i3ct)

This example demonstrates the construction of a vector for the expression of the chimeric Edg receptor Edg 5/3(i3ct) which is designed from Edg 5 and includes two ICD strands (the third intracellular loop and the carboxy terminal strand) from Edg 3.

generated from the primary 50 µl PCR reaction as the template. The first and second DNA, and the third and fourth DNA had overlapping complementary ends. PCR reactions comprised 40 ng/µl of each primer, 0.2 mM dNTPs, 0.02 U/µl VENT™ polymerase in 1× Thermopol™ buffer (Carruthers et al. 1994 JBC 269:29321; adapted from Short Protocols in Molecular Biology. 3$^{rd}$ edition 1995 John Wiley and Sons, Inc. New York, N.Y.). The PCR reactions comprised 35 cycles at an annealing temperature of 55° C. for 45 seconds.

The accuracy of each PCR step was verified by dideoxy sequencing.

TABLE 5

PCR Primers for Generating Chimeric Edg 5 Receptors

| Primer | | Direction | Position | Sequence 5'-3' |
|---|---|---|---|---|
| Edg-5 | (SEQ ID NO:18) | | 1 | CCC/GCG/GTT/AAC/ATG/GGC/AGC/TTG/TAC/TCG |
| Edg-3 | (SEQ ID NO:19) | rev | 1137 | CGC/GGA/TCC/TCA/GTT/GCA/GAA/GAT/CCC |
| E5/3 | (SEQ ID NO:20) | | 864 | CGT/CAT/CTA/CAC/GTG/GGC/CAG/CAA/GGA/GAT/GCG/G |
| E5/3 | (SEQ ID NO:21) | rev | 864 | CCG/CAT/CTC/CTT/GCT/GGC/CCA/CGT/GTA/GAT/GAC/G |
| E5/3 i3 | (SEQ ID NO:22) | | 633 | CAT/CTA/CTG/CGT/GGT/CAA/GTC/CAG/CAG/CCG/TAA/G |
| E5/3 i3 | (SEQ ID NO:23) | rev | 633 | CTT/ACG/GCT/GCT/GGA/CTT/GAC/CAC/GCA/GTA/GAT/G |
| E5/3 i3 | (SEQ ID NO:24) | | 723 | CAC/TGC/TGC/GGA/CCG/TGA/CCA/TCG/TGC/TAG/GCG/TC |
| E1/3 i3 | (SEQ ID NO:25) | rev | 723 | GAC/GCC/TAG/CAC/GAT/GGT/CAC/GGT/CCG/CAG/CAG/TG |

A vector for expressing Edg 5/3(i3ct) was produced by PCR-based, splice-overlap mutagenesis in which the third intracellular strand of Edg 5/3(ct) was replaced with the third intracellular strand of Edg3. DNA encoding the chimeric Edg 5/3(ct) receptor was prepared as described in Example 6.4, above, and DNA encoding Edg 3 was obtained as described in Example 6.1.

A first DNA encoding the portion of Edg 5 from the amino terminus through amino acid 216 was produced by PCR with primers SEQ ID NO:18 and SEQ ID NO:23 using the Edg 5/3(ct) DNA as a template. A second DNA encoding the third intracellular loop of Edg 3 (Edg 3 residues 223–243) was produced by PCR with primers SEQ ID NO:22 and SEQ ID NO:25 using the Edg 3 cDNA as a template. A third DNA encoding the portion of Edg 5/3(ct) from amino acid 234 through the carboxy terminus was produced by PCR with primers SEQ ID NO:24 and SEQ ID NO:19 using the Edg 5/3(ct) DNA as a template. The first and second DNA had overlapping complementary ends, and the second and third DNA had overlapping complementary ends. PCR reactions comprised about 1 ng/µL template, 40 ng/µL each primer, 0.2 mM dNTPs, 0.02 U/µL VENT™ polymerase in 1× Thermopol™ buffer (Mullis, K. et al. 1996. Cold Spring Harbor Symposia on Quantitative Biology 51:263). The PCR reactions comprised 35 cycles at an annealing temperature of 55° C. for 45 seconds.

A fourth DNA encoding a portion of the Edg 5/3(i3ct) chimera was produced in a secondary PCR reaction with primers SEQ ID NO:18 and SEQ ID NO:25 and using 10 µl each of the first and second DNA generated from the primary 50 µl PCR reaction as the template. DNA encoding the full length Edg 5/3(i3ct) chimera was then produced in a tertiary PCR reaction with primers SEQ ID NO:18 and SEQ ID NO:19 and using 10 µl each of the third and fourth DNA

6.6 Preparation of Vector for Expression of Chimeric GPCR Edg 8/4(ct)

This example demonstrates the construction of a vector for the expression of a chimeric Edg receptor, Edg 8/4(ct), which is designed from Edg 8 and includes the carboxy terminal strand from Edg 4 mt.

cDNA encoding the wild type Edg 8 receptor and Edg 4 mt receptor (Accession No. AF011466) were obtained from Dr. Edward Goetzl (UCSF) and subcloned into the pLXSN vector (Clontech Labs, Palo Alto, Calif.).

A vector for expressing Edg 8/4(ct) was produced by PCR-based, splice-overlap mutagenesis in which the carboxy terminal strand of Edg 8 was replaced with the carboxy terminal stand of Edg 4 mt.

In particular, a first DNA encoding all of Edg 8 except the carboxy terminal strand (Edg 8 amino acid residues 1–308) was produced by PCR with primers SEQ ID NO:26 and SEQ ID NO:29 using the Edg 8 cDNA as a template. Primers for the construction of chimeric Edg 8 receptor are listed in Table 6, below. A second DNA encoding the carboxy terminal strand of Edg 4 mt (Edg 4 mt amino acid residues 298–382) was produced by PCR with primers SEQ ID NO:28 and SEQ ID NO:27 using the Edg 4 cDNA as a template. PCR reactions comprised 1 ng/µL template, 40 ng/µL each primer, 0.2 mM dNTPs, 0.02 U/µL VENT™ polymerase in 1× Thermopol™ buffer (Mullis, K. et al. 1996. Cold Spring Harbor Symposia on Quantitative Biology 51:263). The PCR reactions comprised 35 cycles at an annealing temperature of 55° C. for 45 seconds.

DNA encoding the full length Edg 8/4(ct) chimera was produced in a secondary PCR reaction with primers SEQ ID NO:26 and SEQ ID NO:27 and using 10 µl each of the first and second DNA generated from the primary 50 µl PCR reaction as the template. The first and second DNA had overlapping complementary ends. PCR reactions comprised 40 ng/μl of each primer, 0.2 mM dNTPs, 0.02 U/μl VENT™ polymerase in 1×Thermopol™ buffer (Carruthers et al. 1994 JBC 269:29321; adapted from Short Protocols in Molecular Biology. 3$^{rd}$ edition 1995 John Wiley and Sons, Inc. New York, N.Y.). The PCR reactions comprised 35 cycles at an annealing temperature of 55° C. for 45 seconds.

The accuracy of each PCR step was verified by dideoxy sequencing.

(arbitrary units). The cells were contacted with 100 nM of the Edg 1 agonist sphingosine-1-phosphate (S1P) 50 seconds after the start of the assay.

As shown in FIG. 2, cells expressing Edg 1 showed no change in intracellular calcium. In contrast, cells expressing Edg1/3(i3ct) or Edg1/3(i2i3ct) displayed a significant change in intracellular calcium, indicating that these chimeric receptors couple robustly to calcium mobilizing pathways. FIG. 4 demonstrates that Edg 1/3(ct) chimera is also functional, although not as robust as Edg1/3(i3ct) or Edg1/

TABLE 6

PCR Primers for Generating Chimeric Edg 8 Receptors

| Primer |  | Direction | Position | Sequence 5'-3' |
|---|---|---|---|---|
| Edg-8 | (SEQ ID NO:26) |  | 1 | CCC/GCG/GTT/AAC/ATG/GAG/TCG/GGG/CTG/CTG |
| Edg-4-mut | (SEQ ID NO:27) | rev | 1149 | CGC/GGA/TCC/TCA/GTC/CTG/TTG/GTT/GGG |
| E8/4 | (SEQ ID NO:28) |  | 920 | CCA/TCA/TCT/ACA/CGC/TCC/GAG/ATG/CTG/AGA/TGC/G |
| E8/4 | (SEQ ID NO:29) | rev | 920 | CGC/ATC/TCA/GCA/TCT/CGG/AGC/GTG/TAG/ATG/ATG/G |

6.7 Expression of Chimeric GPCRs

This example demonstrates the preparation of cells expressing the chimeric Edg receptors of the above examples.

DNAs encoding Edg1, Edg 1/3(ct), Edg 1/3(i3ct), Edg1/3(i2i3ct), Edg 5/3(i3ct) and Edg 8/4(ct) were co-transfected with pEco-IRES-Puro (obtained from Thomas Quinn, Clontech Labs, Palo Alto, Calif.), which provides an ecotropic envelope for viral replication, into packaging cell line GP-293. Cell line GP-293 has integrated in its genome gag and pol, genes necessary for viral packaging from vesicular stomatitis virus (Clontech Labs., Palo Alto, Calif.).

Media from GP-293 cells was collected and filtered through a 0.45 mm PES syringe filter to remove cell debris. Polybrene (hexadimethrine bromide, Sigma) was added to each virus laden supernatant to a final concentration of 4 mg/ml. After removing the culture medium from the target cells, the virus-laden medium was used to overlay the host cell line HTC4 (rat hepatoma cell line; from Ed Goetzl, UCSF). Following infection, cells were incubated for 18–24 hours. Cells resistant to antibiotic (Geneticin, G418, 400 mg/ml, Sigma) were selected. Clonal populations were selected from the pooled stable cells using a standard limiting dilution technique (adapted from "Antibodies: A Laboratory Manual"; 1988, Harlow, E. and Lane, D., Cold Spring Harbor Laboratory, New York).

6.8 Activity of Chimeric Edg 1 Receptors

This example demonstrates that chimeric Edg 1 receptors of the above examples respond to a Edg 1 agonist by mobilizing intracellular calcium.

HTC4 rat hepatoma cells stably transfected with Edg 1, Edg 1/3(ct), Edg1/3(i3ct) or Edg1/3(i2i3ct) according to Example 6.7 were plated on 384-well plates and loaded with a calcium dye loading kit (Molecular Devices, Sunnyvale, Calif.) for 1 hour at room temperature. Cells were then placed on FLIPR$^{384}$ (Molecular Devices, Sunnyvale, Calif.) and excited by an argon laser at 488 nm. In this assay, fluorescence changes over basal levels indicate an increase in intracellular calcium. In FIG. 2, basal fluorescence is at 0

3(i2i3ct). Thus, the cytoplasmic tail of Edg 3 alone can confer some level of Gαq coupling, and this effect is enhanced by the introduction of additional intracellular loops 3 and 2 (see FIG. 2).

These results demonstrate the effectiveness of Edg chimeras designed from a first Edg receptor and having chimeric ICDs with one, two or three intracellular strands from a second Edg receptor that couples with Gαq. In particular, such chimeras are capable of responding to an agonist of the first Edg receptor by mobilizing intracellular calcium.

6.9 Dose Response of a Chimeric GPCR

This example demonstrates that a chimeric Edg 1 GPCR is capable of mobilizing intracellular calcium in a dose-dependent manner.

HTC4 rat hepatoma cells stably transfected with Edg1/3 (i3ct) according to Example 6.7 were plated on 384-well plates and loaded with a calcium dye loading kit (Molecular Devices, Sunnyvale, Calif.) for 1 hour at room temperature. Cells were then placed on FLIPR$^{384}$ (Molecular Devices, Sunnyvale, Calif.) and excited by an argon laser at 488 nm. Fluorescence changes over basal are seen as an increase in intracellular calcium.

As shown in FIG. 3, the cells displayed a dose dependent response to the Edg 1 agonists sphingosine-1-phosphate ("S1P", EC50~10 nM) and dihydro sphingosine-1-phosphate ("dihydro S1P", EC50~10 nM). The cells also responded to sphigosine phosphoryl choline ("SPC") at higher concentrations. The cells also responded to sphingosylphosphoryl choline ("SPC") at significantly higher concentrations. These results are comparable to the Edg 1 ligand binding profile for these compounds reported in the literature (Van Brocklyn et al., 1998, *J. Cell Biol.* 142:229–240; van Koppen et al., 1996, *J. Biol. Chem.* 271:2082–2087; Hla, 2001, *Prostaglandins and other Lipid Mediators* 64:135–142; Parrill et al., 2000, *J. Biol. Chem.* 275:39379–39384).

6.10 Activity of Chimeric Edg 5 and Chimeric Edg 8 Receptors

This example demonstrates that chimeric Edg 5 and chimeric Edg 8 receptors of the above examples respond to an agonist of Edg 5 and Edg 8 by mobilizing intracellular calcium.

HTC4 rat hepatoma cells stably transfected with Edg5/3 (i3ct) and Edg8/4(ct) according to Example 6.7 were plated on 384-well plates and loaded with a calcium dye loading kit (Molecular Devices, Sunnyvale, Calif.) for 1 hour at room temperature. Cells were then placed on FLIPR$^{384}$ (Molecular Devices, Sunnyvale, Calif.) and excited by an argon laser at 488 nm. In this assay, fluorescence changes over basal levels indicate an increase in intracellular calcium. In FIG. 5, basal fluorescence is at 0 (arbitrary units). The cells were contacted with 100 nM of the Edg 5 and Edg 8 agonist sphingosine-1-phosphate (S1P) 50 seconds after the start of the assay.

FIG. 5 demonstrates that Edg5/3i3 and Edg8/4 mobilize intracellular calcium in response to an agonist of the native Edg 5 or Edg 8 receptor.

These results further demonstrate the effectiveness of Edg chimeras designed from a first Edg receptor and having chimeric ICDs with one or two intracellular strands from a second Edg receptor that couples with Gαq. In particular, such chimeras are capable of responding to an agonist of the first Edg receptor by mobilizing intracellular calcium.

Various embodiments of the invention have been described. The descriptions and examples are intended to be illustrative of the invention and not limiting. Indeed, it will be apparent to those of skill in the art that modifications may be made to the various embodiments of the invention described without departing from the spirit of the invention or scope of the appended claims set forth below.

All references cited herein are hereby incorporated by reference in their entireties.

What is claimed is:

1. A chimeric Edg receptor selected from the group consisting of Edg 1/3(i3ct), Edg 1/3(i2i3ct) Edg 5/13(i3ct) comprising a portion of a first Edg receptor and a portion of a second Edg receptor, wherein the chimeric Edg receptor comprises:
   (a) a non-contiguous replacement of at least one intracellular domain strand of a first Edg receptor;
   (b) with a corresponding strand from a second Edg receptor.

2. A cell comprising the chimeric Edg receptor of claim 1.

3. A method of screening for compounds that bind an Edg receptor comprising:
   a) contacting the chimeric Edg receptor of claim 1 with a compound; and
   b) detecting binding of the compound to the chimeric Edg receptor thereby identifying a compound that binds the first Edg receptor.

4. A method of screening for compounds that modulate the activity of an Edg receptor comprising:
   a) contacting the chimeric Edg receptor of claim 1 with a compound; and
   b) detecting modulation of the activity of the chimeric Edg receptor relative to the activity of the chimeric Edg receptor in the absence of the compound, thereby identifying a compound that modulates the activity of the chimeric Edg receptor.

5. The method of claim 4, wherein the activity of the chimeric Edg receptor is increased.

6. The method of claim 4, wherein the activity of the chimeric Edg receptor is decreased.

7. The method of claim 4, wherein the activity of the chimeric Edg receptor is detected by a calcium mobilization assay.

8. The chimeric Edg receptor of claim 1, which couples with a Gαq protein comprising:
   a) an extracellular domain of a first Edg receptor, wherein the first Edg receptor does not couple with a Gαq protein;
   b) a transmembrane domain of the first Edg receptor, wherein the transmembrane domain is operably linked to the extracellular domain; and
   c) a chimeric intracellular domain comprising an intracellular strand of a second Edg receptor, wherein the intracellular strand of the second Edg receptor couples with a Gαq protein, and the chimelic intracellular domain is operably linked to the transmembrane domain.

9. The chimeric Edg receptor of claim 1, wherein second intracellular loop and the third intracellular loop of the first Edg receptor are replaced with the corresponding strands of the second Edg receptor.

10. The chimeric Edg receptor of claim 1, wherein the second intracellular loop, the third intracellular loop, and the carboxy terminal strand of the first Edg receptor are replaced with the corresponding strands of the second Edg receptor.

11. A chimeric Edg receptor comprising:
   a) an extracellular domain of a first Edg receptor;
   b) a transmembrane domain of the first Edg receptor, wherein the transmembrane domain is operably linked to the extracellular domain; and
   c) a chimeric intracellular domain comprising a third intracellular loop and a carboxy terminal strand of a second Edg receptor, wherein the chimeric intracellular domain is operably linked to the transmembrane domain.

12. The chimeric Edg receptor of claim 11, wherein the first Edg receptor is selected from the group consisting of Edg 1, Edg 5, Edg 6 and Edg 8.

13. The chimeric Edg receptor of claim 11, wherein the second Edg receptor is selected from the group consisting of Edg 2, Edg 3, Edg 4 and Edg 7.

14. A method of screening for compounds that bind an Edg receptor comprising:
   a) contacting the chimeëc Edg receptor of claim 8, 11, 12 or 13 with a compound; and
   b) detecting binding of the compound to the chimeric Edg receptor thereby identifying a compound that binds the first Edg receptor.

15. A method of screening for compounds that modulate the activity of an Edg receptor comprising:
   a) contacting the chimeric Edg receptor of claim 8, 11, 12 or 13 with a compound; and
   b) detecting modulation of the activity of the chimeric Edg receptor relative to the activity of the chimeric Edg receptor in the absence of the compound, thereby identifying a compound that modulates the activity of the chimeric Edg receptor.

16. A nucleic acid encoding a chimeric Edg receptor selected from the group consisting of Edg 1/3(i3ct), Edg 1/3(i2i3ct) and Edg 5/3(i3ct) comprising a portion of a first Edg receptor and a portion of a second Edg receptor, wherein the chimeric Edg receptor comprises:
   (a) a non-contiguous replacement of at least one intracellular domain strand of a first Edg receptor;
   (b) with a corresponding strand from a second Edg receptor.

17. A cell comprising the nucleic acid of claim 16.

* * * * *

SEQUENCE LISTING

```
<160> NUMBER OF SEQ ID NOS: 38

<210> SEQ ID NO 1
<211> LENGTH: 382
<212> TYPE: PRT
<213> ORGANISM: Homo sapiens

<400> SEQUENCE: 1

Met Gly Pro Thr Ser Val Pro Leu Val Lys Ala His Arg Ser Ser Val
1               5                   10                  15

Ser Asp Tyr Val Asn Tyr Asp Ile Ile Val Arg His Tyr Asn Tyr Thr
            20                  25                  30

Gly Lys Leu Asn Ile Ser Ala Asp Lys Glu Asn Ser Ile Lys Leu Thr
        35                  40                  45

Ser Val Val Phe Ile Leu Ile Cys Cys Phe Ile Ile Leu Glu Asn Ile
    50                  55                  60

Phe Val Leu Leu Thr Ile Trp Lys Thr Lys Lys Phe His Arg Pro Met
65                  70                  75                  80

Tyr Tyr Phe Ile Gly Asn Leu Ala Leu Ser Asp Leu Leu Ala Gly Val
                85                  90                  95

Ala Tyr Thr Ala Asn Leu Leu Leu Ser Gly Ala Thr Thr Tyr Lys Leu
            100                 105                 110

Thr Pro Ala Gln Trp Phe Leu Arg Glu Gly Ser Met Phe Val Ala Leu
        115                 120                 125

Ser Ala Ser Val Phe Ser Leu Leu Ala Ile Ala Ile Glu Arg Tyr Ile
    130                 135                 140

Thr Met Leu Lys Met Lys Leu His Asn Gly Ser Asn Asn Phe Arg Leu
145                 150                 155                 160

Phe Leu Leu Ile Ser Ala Cys Trp Val Ile Ser Leu Ile Leu Gly Gly
                165                 170                 175

Leu Pro Ile Met Gly Trp Asn Cys Ile Ser Ala Leu Ser Ser Cys Ser
            180                 185                 190

Thr Val Leu Pro Leu Tyr His Lys His Tyr Ile Leu Phe Cys Thr Thr
        195                 200                 205

Val Phe Thr Leu Leu Leu Leu Ser Ile Val Ile Leu Tyr Cys Arg Ile
    210                 215                 220
```

```
Tyr Ser Leu Val Arg Thr Arg Ser Arg Leu Thr Phe Arg Lys Asn
225                 230                 235                 240

Ile Ser Lys Ala Ser Arg Ser Glu Lys Ser Leu Ala Leu Leu Lys
            245                 250                 255

Thr Val Ile Ile Val Leu Ser Val Phe Ile Ala Cys Trp Ala Pro Leu
        260                 265                 270

Phe Ile Leu Leu Leu Asp Val Gly Cys Lys Val Lys Thr Cys Asp
        275                 280                 285

Ile Leu Phe Arg Ala Glu Tyr Phe Leu Val Leu Ala Val Leu Asn Ser
        290                 295                 300

Gly Thr Asn Pro Ile Ile Tyr Thr Leu Thr Asn Lys Glu Met Arg Arg
305                 310                 315                 320

Ala Phe Ile Arg Ile Met Ser Cys Cys Lys Cys Pro Ser Gly Asp Ser
                325                 330                 335

Ala Gly Lys Phe Lys Arg Pro Ile Ile Ala Gly Met Glu Phe Ser Arg
                340                 345                 350

Ser Lys Ser Asp Asn Ser Ser His Pro Gln Lys Asp Glu Gly Asp Asn
            355                 360                 365

Pro Glu Thr Ile Met Ser Ser Gly Asn Val Asn Ser Ser Ser
        370                 375                 380

<210> SEQ ID NO 2
<211> LENGTH: 378
<212> TYPE: PRT
<213> ORGANISM: Homo sapiens

<400> SEQUENCE: 2

Met Ala Thr Ala Leu Pro Pro Arg Leu Gln Pro Val Arg Gly Asn Glu
1               5                   10                  15

Thr Leu Arg Glu His Tyr Gln Tyr Val Gly Lys Leu Ala Gly Arg Leu
            20                  25                  30

Lys Glu Ala Ser Glu Gly Ser Thr Leu Thr Thr Val Leu Phe Leu Val
        35                  40                  45

Ile Cys Ser Phe Ile Val Leu Glu Asn Leu Met Val Leu Ile Ala Ile
    50                  55                  60

Trp Lys Asn Asn Lys Phe His Asn Arg Met Tyr Phe Phe Ile Gly Asn
65                  70                  75                  80

Leu Ala Leu Cys Asp Leu Leu Ala Gly Ile Ala Tyr Lys Val Asn Ile
                85                  90                  95

Leu Met Ser Gly Lys Lys Thr Phe Ser Leu Ser Pro Thr Val Trp Phe
            100                 105                 110

Leu Arg Glu Gly Ser Met Phe Val Ala Leu Gly Ala Ser Thr Cys Ser
        115                 120                 125

Leu Leu Ala Ile Ala Ile Glu Arg His Leu Thr Met Ile Lys Met Arg
    130                 135                 140

Pro Tyr Asp Ala Asn Lys Arg His Arg Val Phe Leu Leu Ile Gly Met
145                 150                 155                 160

Cys Trp Leu Ile Ala Phe Thr Leu Gly Ala Leu Pro Ile Leu Gly Trp
                165                 170                 175

Asn Cys Leu His Asn Leu Pro Asp Cys Ser Thr Ile Leu Pro Leu Tyr
            180                 185                 190

Ser Lys Lys Tyr Ile Ala Phe Cys Ile Ser Ile Phe Thr Ala Ile Leu
        195                 200                 205

Val Thr Ile Val Ile Leu Tyr Ala Arg Ile Tyr Phe Leu Val Lys Ser
    210                 215                 220
```

```
Ser Ser Arg Lys Val Ala Asn His Asn Asn Ser Glu Arg Ser Met Ala
225                 230                 235                 240

Leu Leu Arg Thr Val Val Ile Val Val Ser Val Phe Ile Ala Cys Trp
                245                 250                 255

Ser Pro Leu Phe Ile Leu Phe Leu Ile Asp Val Ala Cys Arg Val Gln
                260                 265                 270

Ala Cys Pro Ile Leu Phe Lys Ala Gln Trp Phe Ile Val Leu Ala Val
            275                 280                 285

Leu Asn Ser Ala Met Asn Pro Val Ile Tyr Thr Leu Ala Ser Lys Glu
        290                 295                 300

Met Arg Arg Ala Phe Phe Arg Leu Val Cys Asn Cys Leu Val Arg Gly
305                 310                 315                 320

Arg Gly Ala Arg Ala Ser Pro Ile Gln Pro Ala Leu Asp Pro Ser Arg
                325                 330                 335

Ser Lys Ser Ser Ser Asn Asn Ser Ser His Ser Pro Lys Val Lys
                340                 345                 350

Glu Asp Leu Pro His Thr Asp Pro Ser Ser Cys Ile Met Asp Lys Asn
                355                 360                 365

Ala Ala Leu Gln Asn Gly Ile Phe Cys Asn
        370                 375

<210> SEQ ID NO 3
<211> LENGTH: 391
<212> TYPE: PRT
<213> ORGANISM: Artificial Sequence
<220> FEATURE:
<223> OTHER INFORMATION: Description of artificial sequence: Chimeric
      Edg receptor

<400> SEQUENCE: 3

Met Gly Pro Thr Ser Val Pro Leu Val Lys Ala His Arg Ser Ser Val
1               5                   10                  15

Ser Asp Tyr Val Asn Tyr Asp Ile Ile Val Arg His Tyr Asn Tyr Thr
                20                  25                  30

Gly Lys Leu Asn Ile Ser Ala Asp Lys Glu Asn Ser Ile Lys Leu Thr
            35                  40                  45

Ser Val Val Phe Ile Leu Ile Cys Cys Phe Ile Ile Leu Glu Asn Ile
        50                  55                  60

Phe Val Leu Leu Thr Ile Trp Lys Thr Lys Lys Phe His Arg Pro Met
65                  70                  75                  80

Tyr Tyr Phe Ile Gly Asn Leu Ala Leu Ser Asp Leu Leu Ala Gly Val
                85                  90                  95

Ala Tyr Thr Ala Asn Leu Leu Leu Ser Gly Ala Thr Thr Tyr Lys Leu
            100                 105                 110

Thr Pro Ala Gln Trp Phe Leu Arg Glu Gly Ser Met Phe Val Ala Leu
        115                 120                 125

Ser Ala Ser Val Phe Ser Leu Leu Ala Ile Ala Ile Glu Arg Tyr Ile
    130                 135                 140

Thr Met Leu Lys Met Lys Leu His Asn Gly Ser Asn Asn Phe Arg Leu
145                 150                 155                 160

Phe Leu Leu Ile Ser Ala Cys Trp Val Ile Ser Leu Ile Leu Gly Gly
                165                 170                 175

Leu Pro Ile Met Gly Trp Asn Cys Ile Ser Ala Leu Ser Ser Cys Ser
            180                 185                 190

Thr Val Leu Pro Leu Tyr His Lys His Tyr Ile Leu Phe Cys Thr Thr
```

-continued

```
            195                 200                 205
Val Phe Thr Leu Leu Leu Ser Ile Val Ile Leu Tyr Cys Arg Ile
            210                 215                 220

Tyr Ser Leu Val Arg Thr Arg Ser Arg Arg Leu Thr Phe Arg Lys Asn
225                 230                 235                 240

Ile Ser Lys Ala Ser Arg Ser Glu Lys Ser Leu Ala Leu Leu Lys
                245                 250                 255

Thr Val Ile Ile Val Leu Ser Val Phe Ile Ala Cys Trp Ala Pro Leu
            260                 265                 270

Phe Ile Leu Leu Leu Asp Val Gly Cys Lys Val Lys Thr Cys Asp
            275                 280                 285

Ile Leu Phe Arg Ala Glu Tyr Phe Leu Val Leu Ala Val Leu Asn Ser
            290                 295                 300

Gly Thr Asn Pro Ile Ile Tyr Thr Leu Thr Ser Lys Glu Met Arg Arg
305                 310                 315                 320

Ala Phe Phe Arg Leu Val Cys Asn Cys Leu Val Arg Gly Arg Gly Ala
                325                 330                 335

Arg Ala Ser Pro Ile Gln Pro Ala Leu Asp Pro Ser Arg Ser Lys Ser
                340                 345                 350

Ser Ser Ser Asn Asn Ser Ser His Ser Pro Lys Val Lys Glu Asp Leu
                355                 360                 365

Pro His Thr Asp Pro Ser Ser Cys Ile Met Asp Lys Asn Ala Ala Leu
            370                 375                 380

Gln Asn Gly Ile Phe Cys Asn
385                 390

<210> SEQ ID NO 4
<211> LENGTH: 384
<212> TYPE: PRT
<213> ORGANISM: Artificial Sequence
<220> FEATURE:
<223> OTHER INFORMATION: Description of artificial sequence:  Chimeric
      Edg receptor

<400> SEQUENCE: 4

Met Gly Pro Thr Ser Val Pro Leu Val Lys Ala His Arg Ser Ser Val
1               5                   10                  15

Ser Asp Tyr Val Asn Tyr Asp Ile Ile Val Arg His Tyr Asn Tyr Thr
            20                  25                  30

Gly Lys Leu Asn Ile Ser Ala Asp Lys Glu Asn Ser Ile Lys Leu Thr
        35                  40                  45

Ser Val Val Phe Ile Leu Ile Cys Cys Phe Ile Ile Leu Glu Asn Ile
    50                  55                  60

Phe Val Leu Leu Thr Ile Trp Lys Thr Lys Lys Phe His Arg Pro Met
65                  70                  75                  80

Tyr Tyr Phe Ile Gly Asn Leu Ala Leu Ser Asp Leu Leu Ala Gly Val
                85                  90                  95

Ala Tyr Thr Ala Asn Leu Leu Leu Ser Gly Ala Thr Thr Tyr Lys Leu
            100                 105                 110

Thr Pro Ala Gln Trp Phe Leu Arg Glu Gly Ser Met Phe Val Ala Leu
        115                 120                 125

Ser Ala Ser Val Phe Ser Leu Leu Ala Ile Ala Ile Glu Arg Tyr Ile
    130                 135                 140

Thr Met Leu Lys Met Lys Leu His Asn Gly Ser Asn Asn Phe Arg Leu
145                 150                 155                 160
```

-continued

Phe Leu Leu Ile Ser Ala Cys Trp Val Ile Ser Ile Leu Gly Gly
                165                 170                 175

Leu Pro Ile Met Gly Trp Asn Cys Ile Ser Ala Leu Ser Ser Cys Ser
            180                 185                 190

Thr Val Leu Pro Leu Tyr His Lys His Tyr Ile Leu Phe Cys Thr Thr
        195                 200                 205

Val Phe Thr Leu Leu Leu Ser Ile Val Ile Leu Tyr Cys Arg Ile
210                 215                 220

Tyr Ser Leu Val Arg Ser Ser Arg Lys Val Ala Asn His Asn Asn
225                 230                 235                 240

Ser Glu Arg Ser Met Ala Leu Leu Arg Thr Val Ile Ile Val Leu Ser
                245                 250                 255

Val Phe Ile Ala Cys Trp Ala Pro Leu Phe Ile Leu Leu Leu Leu Asp
            260                 265                 270

Val Gly Cys Lys Val Lys Thr Cys Asp Ile Leu Phe Arg Ala Glu Tyr
        275                 280                 285

Phe Leu Val Leu Ala Val Leu Asn Ser Gly Thr Asn Pro Ile Ile Tyr
290                 295                 300

Thr Leu Thr Ser Lys Glu Met Arg Arg Ala Phe Phe Arg Leu Val Cys
305                 310                 315                 320

Asn Cys Leu Val Arg Gly Arg Gly Ala Arg Ala Ser Pro Ile Gln Pro
                325                 330                 335

Ala Leu Asp Pro Ser Arg Ser Lys Ser Ser Ser Ser Asn Asn Ser Ser
            340                 345                 350

His Ser Pro Lys Val Lys Glu Asp Leu Pro His Thr Asp Pro Ser Ser
        355                 360                 365

Cys Ile Met Asp Lys Asn Ala Ala Leu Gln Asn Gly Ile Phe Cys Asn
370                 375                 380

<210> SEQ ID NO 5
<211> LENGTH: 384
<212> TYPE: PRT
<213> ORGANISM: Artificial Sequence
<220> FEATURE:
<223> OTHER INFORMATION: Description of artificial sequence: Chimeric
      Edg receptor

<400> SEQUENCE: 5

Met Gly Pro Thr Ser Val Pro Leu Val Lys Ala His Arg Ser Ser Val
1               5                   10                  15

Ser Asp Tyr Val Asn Tyr Asp Ile Ile Val Arg His Tyr Asn Tyr Thr
            20                  25                  30

Gly Lys Leu Asn Ile Ser Ala Asp Lys Glu Asn Ser Ile Lys Leu Thr
        35                  40                  45

Ser Val Val Phe Ile Leu Ile Cys Cys Phe Ile Ile Leu Glu Asn Ile
50                  55                  60

Phe Val Leu Leu Thr Ile Trp Lys Thr Lys Lys Phe His Arg Pro Met
65                  70                  75                  80

Tyr Tyr Phe Ile Gly Asn Leu Ala Leu Ser Asp Leu Leu Ala Gly Val
                85                  90                  95

Ala Tyr Thr Ala Asn Leu Leu Leu Ser Gly Ala Thr Thr Tyr Lys Leu
            100                 105                 110

Thr Pro Ala Gln Trp Phe Leu Arg Glu Gly Ser Met Phe Val Ala Leu
        115                 120                 125

Ser Ala Ser Val Phe Ser Leu Leu Ala Ile Ala Ile Glu Arg His Leu
130                 135                 140

Thr Met Ile Lys Met Arg Pro Tyr Asp Ala Asn Lys Arg His Arg Leu
145                 150                 155                 160

Phe Leu Leu Ile Ser Ala Cys Trp Val Ile Ser Leu Ile Leu Gly Gly
                165                 170                 175

Leu Pro Ile Met Gly Trp Asn Cys Ile Ser Ala Leu Ser Ser Cys Ser
            180                 185                 190

Thr Val Leu Pro Leu Tyr His Lys His Tyr Ile Leu Phe Cys Thr Thr
        195                 200                 205

Val Phe Thr Leu Leu Leu Ser Ile Val Ile Leu Tyr Cys Arg Ile
    210                 215                 220

Tyr Ser Leu Val Arg Ser Ser Arg Lys Val Ala Asn His Asn Asn
225                 230                 235                 240

Ser Glu Arg Ser Met Ala Leu Leu Arg Thr Val Ile Ile Val Leu Ser
                245                 250                 255

Val Phe Ile Ala Cys Trp Ala Pro Leu Phe Ile Leu Leu Leu Asp
            260                 265                 270

Val Gly Cys Lys Val Lys Thr Cys Asp Ile Leu Phe Arg Ala Glu Tyr
        275                 280                 285

Phe Leu Val Leu Ala Val Leu Asn Ser Gly Thr Asn Pro Ile Ile Tyr
    290                 295                 300

Thr Leu Thr Ser Lys Glu Met Arg Arg Ala Phe Phe Arg Leu Val Cys
305                 310                 315                 320

Asn Cys Leu Val Arg Gly Arg Gly Ala Arg Ala Ser Pro Ile Gln Pro
                325                 330                 335

Ala Leu Asp Pro Ser Arg Ser Lys Ser Ser Ser Ser Asn Asn Ser Ser
            340                 345                 350

His Ser Pro Lys Val Lys Glu Asp Leu Pro His Thr Asp Pro Ser Ser
        355                 360                 365

Cys Ile Met Asp Lys Asn Ala Ala Leu Gln Asn Gly Ile Phe Cys Asn
    370                 375                 380

<210> SEQ ID NO 6
<211> LENGTH: 30
<212> TYPE: DNA
<213> ORGANISM: Artificial Sequence
<220> FEATURE:
<223> OTHER INFORMATION: Description of artificial sequence: Primer for
      generating chimeric Edg 1 receptors

<400> SEQUENCE: 6
cccgcggtta acatggggcc caccagcgtc                                    30

<210> SEQ ID NO 7
<211> LENGTH: 27
<212> TYPE: DNA
<213> ORGANISM: Artificial Sequence
<220> FEATURE:
<223> OTHER INFORMATION: Description of artificial sequence: Primer for
      generating chimeric Edg 1 receptors

<400> SEQUENCE: 7
cgcggatcct cagttgcaga agatccc                                       27

<210> SEQ ID NO 8
<211> LENGTH: 34
<212> TYPE: DNA
<213> ORGANISM: Artificial Sequence
<220> FEATURE:
<223> OTHER INFORMATION: Description of artificial sequence: Primer for generating chimeric Edg 1 receptors

<400> SEQUENCE: 8
catttacact ctgaccagca aggagatgcg gcgg                                34

<210> SEQ ID NO 9
<211> LENGTH: 34
<212> TYPE: DNA
<213> ORGANISM: Artificial Sequence
<220> FEATURE:
<223> OTHER INFORMATION: Description of artificial sequence: Primer for
      generating chimeric Edg 1 receptors

<400> SEQUENCE: 9
ccgcatctcc ttgctggtca gagtgtaaat gatg                                34

<210> SEQ ID NO 10
<211> LENGTH: 34
<212> TYPE: DNA
<213> ORGANISM: Artificial Sequence
<220> FEATURE:
<223> OTHER INFORMATION: Description of artificial sequence: Primer for
      generating chimeric Edg 1 receptors

<400> SEQUENCE: 10
gtctcctcgc catcgccatc gagcggcact tgac                                34

<210> SEQ ID NO 11
<211> LENGTH: 33
<212> TYPE: DNA
<213> ORGANISM: Artificial Sequence
<220> FEATURE:
<223> OTHER INFORMATION: Description of artificial sequence: Primer for
      generating chimeric Edg 1 receptors

<400> SEQUENCE: 11
gtcaagtgcc gctcgatggc gatggcgagg aga                                 33

<210> SEQ ID NO 12
<211> LENGTH: 34
<212> TYPE: DNA
<213> ORGANISM: Artificial Sequence
<220> FEATURE:
<223> OTHER INFORMATION: Description of artificial sequence: Primer for
      generating chimeric Edg 1 receptors

<400> SEQUENCE: 12
cgccaacaag aggcaccgcc tcttcctgct aatc                                34

<210> SEQ ID NO 13
<211> LENGTH: 34
<212> TYPE: DNA
<213> ORGANISM: Artificial Sequence
<220> FEATURE:
<223> OTHER INFORMATION: Description of artificial sequence: Primer for
      generating chimeric Edg 1 receptors

<400> SEQUENCE: 13
gattagcagg aagaggcggt gcctcttgtt ggcg                                34

<210> SEQ ID NO 14
<211> LENGTH: 34
<212> TYPE: DNA
<213> ORGANISM: Artificial Sequence
<220> FEATURE:
<223> OTHER INFORMATION: Description of artificial sequence: Primer for
      generating chimeric Edg 1 receptors

```
<400> SEQUENCE: 14
ctactccttg gtcaggtcca gcagccgtaa ggtg                              34

<210> SEQ ID NO 15
<211> LENGTH: 34
<212> TYPE: DNA
<213> ORGANISM: Artificial Sequence
<220> FEATURE:
<223> OTHER INFORMATION: Description of artificial sequence: Primer for
      generating chimeric Edg 1 receptors

<400> SEQUENCE: 15
caccttacgg ctgctggacc tgaccaagga gtag                              34

<210> SEQ ID NO 16
<211> LENGTH: 35
<212> TYPE: DNA
<213> ORGANISM: Artificial Sequence
<220> FEATURE:
<223> OTHER INFORMATION: Description of artificial sequence: Primer for
      generating chimeric Edg 1 receptors

<400> SEQUENCE: 16
cactgctgcg gaccgtgatt atcgtcctga gcgtc                             35

<210> SEQ ID NO 17
<211> LENGTH: 35
<212> TYPE: DNA
<213> ORGANISM: Artificial Sequence
<220> FEATURE:
<223> OTHER INFORMATION: Description of artificial sequence: Primer for
      generating chimeric Edg 1 receptors

<400> SEQUENCE: 17
gacgctcagg acgataatca cggtccgcag cagtg                             35

<210> SEQ ID NO 18
<211> LENGTH: 30
<212> TYPE: DNA
<213> ORGANISM: Artificial Sequence
<220> FEATURE:
<223> OTHER INFORMATION: Description of artificial sequence: Primer for
      generating chimeric Edg 5 receptors

<400> SEQUENCE: 18
cccgcggtta acatgggcag cttgtactcg                                   30

<210> SEQ ID NO 19
<211> LENGTH: 27
<212> TYPE: DNA
<213> ORGANISM: Artificial Sequence
<220> FEATURE:
<223> OTHER INFORMATION: Description of artificial sequence: Primer for
      generating chimeric Edg 5 receptors

<400> SEQUENCE: 19
cgcggatcct cagttgcaga agatccc                                      27

<210> SEQ ID NO 20
<211> LENGTH: 34
<212> TYPE: DNA
<213> ORGANISM: Artificial Sequence
<220> FEATURE:
<223> OTHER INFORMATION: Description of artificial sequence: Primer for
      generating chimeric Edg 5 receptors
```

-continued

```
<400> SEQUENCE: 20
cgtcatctac acgtgggcca gcaaggagat gcgg                                34

<210> SEQ ID NO 21
<211> LENGTH: 34
<212> TYPE: DNA
<213> ORGANISM: Artificial Sequence
<220> FEATURE:
<223> OTHER INFORMATION: Description of artificial sequence: Primer for
      generating chimeric Edg 5 receptors

<400> SEQUENCE: 21
ccgcatctcc ttgctggccc acgtgtagat gacg                                34

<210> SEQ ID NO 22
<211> LENGTH: 34
<212> TYPE: DNA
<213> ORGANISM: Artificial Sequence
<220> FEATURE:
<223> OTHER INFORMATION: Description of artificial sequence: Primer for
      generating chimeric Edg 5 receptors

<400> SEQUENCE: 22
catctactgc gtggtcaagt ccagcagccg taag                                34

<210> SEQ ID NO 23
<211> LENGTH: 34
<212> TYPE: DNA
<213> ORGANISM: Artificial Sequence
<220> FEATURE:
<223> OTHER INFORMATION: Description of artificial sequence: Primer for
      generating chimeric Edg 5 receptors

<400> SEQUENCE: 23
cttacggctg ctggacttga ccacgcagta gatg                                34

<210> SEQ ID NO 24
<211> LENGTH: 35
<212> TYPE: DNA
<213> ORGANISM: Artificial Sequence
<220> FEATURE:
<223> OTHER INFORMATION: Description of artificial sequence: Primer for
      generating chimeric Edg 5 receptors

<400> SEQUENCE: 24
cactgctgcg gaccgtgacc atcgtgctag gcgtc                               35

<210> SEQ ID NO 25
<211> LENGTH: 35
<212> TYPE: DNA
<213> ORGANISM: Artificial Sequence
<220> FEATURE:
<223> OTHER INFORMATION: Description of artificial sequence: Primer for
      generating chimeric Edg 5 receptors

<400> SEQUENCE: 25
gacgcctagc acgatggtca cggtccgcag cagtg                               35

<210> SEQ ID NO 26
<211> LENGTH: 30
<212> TYPE: DNA
<213> ORGANISM: Artificial Sequence
<220> FEATURE:
<223> OTHER INFORMATION: Description of artificial sequence: Primer for
      generating chimeric Edg 8 receptors

<400> SEQUENCE: 26
```

-continued cccgcggtta acatggagtc ggggctgctg                                              30

<210> SEQ ID NO 27
<211> LENGTH: 27
<212> TYPE: DNA
<213> ORGANISM: Artificial Sequence
<220> FEATURE:
<223> OTHER INFORMATION: Description of artificial sequence: Primer for
      generating chimeric Edg 8 receptors

<400> SEQUENCE: 27
cgcggatcct cagtcctgtt ggttggg                                                 27

<210> SEQ ID NO 28
<211> LENGTH: 34
<212> TYPE: DNA
<213> ORGANISM: Artificial Sequence
<220> FEATURE:
<223> OTHER INFORMATION: Description of artificial sequence: Primer for
      generating chimeric Edg 8 receptors

<400> SEQUENCE: 28
ccatcatcta cacgctccga gatgctgaga tgcg                                         34

<210> SEQ ID NO 29
<211> LENGTH: 34
<212> TYPE: DNA
<213> ORGANISM: Artificial Sequence
<220> FEATURE:
<223> OTHER INFORMATION: Description of artificial sequence: Primer for
      generating chimeric Edg 8 receptors

<400> SEQUENCE: 29
cgcatctcag catctcggag cgtgtagatg atgg                                         34

<210> SEQ ID NO 30
<211> LENGTH: 364
<212> TYPE: PRT
<213> ORGANISM: Homo sapiens

<400> SEQUENCE: 30

Met Ala Ala Ile Ser Thr Ser Ile Pro Val Ile Ser Gln Pro Gln Phe
1               5                   10                  15

Thr Ala Met Asn Glu Pro Gln Cys Phe Tyr Asn Glu Ser Ile Ala Phe
            20                  25                  30

Phe Tyr Asn Arg Ser Gly Lys His Leu Ala Thr Glu Trp Asn Thr Val
        35                  40                  45

Ser Lys Leu Val Met Gly Leu Gly Ile Thr Val Cys Ile Phe Ile Met
    50                  55                  60

Leu Ala Asn Leu Leu Val Met Val Ala Ile Tyr Val Asn Arg Arg Phe
65                  70                  75                  80

His Phe Pro Ile Tyr Tyr Leu Met Ala Asn Leu Ala Ala Ala Asp Phe
                85                  90                  95

Phe Ala Gly Leu Ala Tyr Phe Tyr Leu Met Phe Asn Thr Gly Pro Asn
            100                 105                 110

Thr Arg Arg Leu Thr Val Ser Thr Trp Leu Leu Arg Gln Gly Leu Ile
        115                 120                 125

Asp Thr Ser Leu Thr Ala Ser Val Ala Asn Leu Leu Ala Ile Ala Ile
    130                 135                 140

Glu Arg His Ile Thr Val Phe Arg Met Gln Leu His Thr Arg Met Ser
145                 150                 155                 160

Asn Arg Arg Val Val Val Ile Val Ile Trp Thr Met Ala Ile
            165                 170                 175

Val Met Gly Ala Ile Pro Ser Val Gly Trp Asn Cys Ile Cys Asp Ile
            180                 185                 190

Glu Asn Cys Ser Asn Met Ala Pro Leu Tyr Ser Asp Ser Tyr Leu Val
            195                 200                 205

Phe Trp Ala Ile Phe Asn Leu Val Thr Phe Val Met Val Val Leu
    210                 215                 220

Tyr Ala His Ile Phe Gly Tyr Val Arg Gln Arg Thr Met Arg Met Ser
225                 230                 235                 240

Arg His Ser Ser Gly Pro Arg Arg Asn Arg Asp Thr Met Met Ser Leu
                245                 250                 255

Leu Lys Thr Val Val Ile Val Leu Gly Ala Phe Ile Ile Cys Trp Thr
            260                 265                 270

Pro Gly Leu Val Leu Leu Leu Asp Val Cys Cys Pro Gln Cys Asp
    275                 280                 285

Val Leu Ala Tyr Glu Lys Phe Phe Leu Leu Leu Ala Glu Phe Asn Ser
    290                 295                 300

Ala Met Asn Pro Ile Ile Tyr Ser Tyr Arg Asp Lys Glu Met Ser Ala
305                 310                 315                 320

Thr Phe Arg Gln Ile Leu Cys Cys Gln Arg Ser Glu Asn Pro Thr Gly
                325                 330                 335

Pro Thr Glu Gly Ser Asp Arg Ser Ala Ser Ser Leu Asn His Thr Ile
            340                 345                 350

Leu Ala Gly Val His Ser Asn Asp His Ser Val Val
            355                 360

<210> SEQ ID NO 31
<211> LENGTH: 351
<212> TYPE: PRT
<213> ORGANISM: Homo sapiens

<400> SEQUENCE: 31

Met Val Ile Met Gly Gln Cys Tyr Tyr Asn Glu Thr Ile Gly Phe Phe
1               5                   10                  15

Tyr Asn Asn Ser Gly Lys Glu Leu Ser Ser His Trp Arg Pro Lys Asp
            20                  25                  30

Val Val Val Val Ala Leu Gly Leu Thr Val Ser Val Leu Val Leu Leu
        35                  40                  45

Thr Asn Leu Leu Val Ile Ala Ala Ile Ala Ser Asn Arg Arg Phe His
    50                  55                  60

Gln Pro Ile Tyr Tyr Leu Leu Gly Asn Leu Ala Ala Ala Asp Leu Phe
65                  70                  75                  80

Ala Gly Val Ala Tyr Leu Phe Leu Met Phe His Thr Gly Pro Arg Thr
                85                  90                  95

Ala Arg Leu Ser Leu Glu Gly Trp Phe Leu Arg Gln Gly Leu Leu Asp
            100                 105                 110

Thr Ser Leu Thr Ala Ser Val Ala Thr Leu Leu Ala Ile Ala Val Glu
        115                 120                 125

Arg His Arg Ser Val Met Ala Val Gln Leu His Ser Arg Leu Pro Arg
    130                 135                 140

Gly Arg Val Val Met Leu Ile Val Gly Val Trp Val Ala Ala Leu Gly
145                 150                 155                 160

Leu Gly Leu Leu Pro Ala His Ser Trp His Cys Leu Cys Ala Leu Asp

```
                        165                 170                 175
Arg Cys Ser Arg Met Ala Pro Leu Leu Ser Arg Ser Tyr Leu Ala Val
                180                 185                 190

Trp Ala Leu Ser Ser Leu Leu Val Phe Leu Leu Met Val Ala Val Tyr
            195                 200                 205

Thr Arg Ile Phe Phe Tyr Val Arg Arg Val Gln Arg Met Ala Glu
        210                 215                 220

His Val Ser Cys His Pro Arg Tyr Arg Glu Thr Thr Leu Ser Leu Val
225                 230                 235                 240

Lys Thr Val Val Ile Ile Leu Gly Ala Phe Val Cys Trp Thr Pro
                245                 250                 255

Gly Gln Val Val Leu Leu Asp Gly Leu Gly Cys Glu Ser Cys Asn
            260                 265                 270

Val Leu Ala Val Glu Lys Tyr Phe Leu Leu Ala Glu Ala Asn Ser
        275                 280                 285

Leu Val Asn Ala Ala Val Tyr Ser Cys Arg Asp Ala Glu Met Arg Arg
    290                 295                 300

Thr Phe Arg Arg Leu Leu Cys Cys Ala Cys Leu Arg Gln Ser Thr Arg
305                 310                 315                 320

Glu Ser Val His Tyr Thr Ser Ser Ala Gln Gly Gly Ala Ser Thr Arg
                325                 330                 335

Ile Met Leu Pro Glu Asn Gly His Pro Leu Met Asp Ser Thr Leu
                340                 345                 350

<210> SEQ ID NO 32
<211> LENGTH: 382
<212> TYPE: PRT
<213> ORGANISM: Homo sapiens

<400> SEQUENCE: 32

Met Val Ile Met Gly Gln Cys Tyr Tyr Asn Glu Thr Ile Gly Phe Phe
1               5                   10                  15

Tyr Asn Asn Ser Gly Lys Glu Leu Ser Ser His Trp Arg Pro Lys Asp
            20                  25                  30

Val Val Val Val Ala Leu Gly Leu Thr Val Ser Val Leu Val Leu Leu
        35                  40                  45

Thr Asn Leu Leu Val Ile Ala Ala Ile Ala Ser Asn Arg Arg Phe His
    50                  55                  60

Gln Pro Ile Tyr Tyr Leu Leu Gly Asn Leu Ala Ala Ala Asp Leu Phe
65                  70                  75                  80

Ala Gly Val Ala Tyr Leu Phe Leu Met Phe His Thr Gly Pro Arg Thr
                85                  90                  95

Ala Arg Leu Ser Leu Glu Gly Trp Phe Leu Arg Gln Gly Leu Leu Asp
            100                 105                 110

Thr Ser Leu Thr Ala Ser Val Ala Thr Leu Leu Ala Ile Ala Val Glu
        115                 120                 125

Arg His Arg Ser Val Met Ala Val Gln Leu His Ser Arg Leu Pro Arg
    130                 135                 140

Gly Arg Val Val Met Leu Ile Val Gly Val Trp Val Ala Ala Leu Gly
145                 150                 155                 160

Leu Gly Leu Leu Pro Ala His Ser Trp His Cys Leu Cys Ala Leu Asp
                165                 170                 175

Arg Cys Ser Arg Met Ala Pro Leu Leu Ser Arg Ser Tyr Leu Ala Val
            180                 185                 190
```

```
Trp Ala Leu Ser Ser Leu Leu Val Phe Leu Leu Met Val Ala Val Tyr
            195                 200                 205

Thr Arg Ile Phe Phe Tyr Val Arg Arg Val Gln Arg Met Ala Glu
    210                 215                 220

His Val Ser Cys His Pro Arg Tyr Arg Glu Thr Thr Leu Ser Leu Val
225                 230                 235                 240

Lys Thr Val Val Ile Ile Leu Gly Ala Phe Val Val Cys Trp Thr Pro
                245                 250                 255

Gly Gln Val Val Leu Leu Leu Asp Gly Leu Gly Cys Glu Ser Cys Asn
            260                 265                 270

Val Leu Ala Val Glu Lys Tyr Phe Leu Leu Leu Ala Glu Ala Asn Ser
            275                 280                 285

Leu Val Asn Ala Ala Val Tyr Ser Cys Arg Asp Ala Glu Met Arg Arg
            290                 295                 300

Thr Phe Arg Arg Leu Leu Cys Cys Ala Cys Leu Arg Gln Ser Thr Arg
305                 310                 315                 320

Glu Ser Val His Tyr Thr Ser Ser Ala Gln Gly Gly Ala Ser Thr Arg
                325                 330                 335

Ile Met Leu Pro Glu Asn Gly His Pro Leu Met Thr Pro Pro Phe Ser
            340                 345                 350

Tyr Leu Glu Leu Gln Arg Tyr Ala Ala Ser Asn Lys Ser Thr Ala Pro
            355                 360                 365

Asp Asp Leu Trp Val Leu Leu Ala Gln Pro Asn Gln Gln Asp
            370                 375                 380

<210> SEQ ID NO 33
<211> LENGTH: 353
<212> TYPE: PRT
<213> ORGANISM: Homo sapiens

<400> SEQUENCE: 33

Met Gly Ser Leu Tyr Ser Glu Tyr Leu Asn Pro Asn Lys Val Gln Glu
1               5                   10                  15

His Tyr Asn Tyr Thr Lys Glu Thr Leu Glu Thr Gln Glu Thr Thr Ser
            20                  25                  30

Arg Gln Val Ala Ser Ala Phe Ile Val Ile Leu Cys Cys Ala Ile Val
        35                  40                  45

Val Glu Asn Leu Leu Val Leu Ile Ala Val Ala Arg Asn Ser Lys Phe
    50                  55                  60

His Ser Ala Met Tyr Leu Phe Leu Gly Asn Leu Ala Ala Ser Asp Leu
65                  70                  75                  80

Leu Ala Gly Val Ala Phe Val Ala Asn Thr Leu Leu Ser Gly Ser Val
                85                  90                  95

Thr Leu Arg Leu Thr Pro Val Gln Trp Phe Ala Arg Glu Gly Ser Ala
            100                 105                 110

Ser Ile Thr Leu Ser Ala Ser Val Phe Ser Leu Leu Ala Ile Ala Ile
        115                 120                 125

Glu Arg His Val Ala Ile Ala Lys Val Lys Leu Tyr Gly Ser Asp Lys
    130                 135                 140

Ser Cys Arg Met Leu Leu Leu Ile Gly Ala Ser Trp Leu Ile Ser Leu
145                 150                 155                 160

Val Leu Gly Gly Leu Pro Ile Leu Gly Trp Asn Cys Leu Gly His Leu
                165                 170                 175

Glu Ala Cys Ser Thr Val Leu Pro Leu Tyr Ala Lys His Tyr Val Leu
            180                 185                 190
```

-continued

Cys Val Val Thr Ile Phe Ser Ile Ile Leu Leu Ala Ile Val Ala Leu
        195                 200                 205

Tyr Val Arg Ile Tyr Cys Val Val Arg Ser Ser His Ala Asp Met Ala
    210                 215                 220

Ala Pro Gln Thr Leu Ala Leu Leu Lys Thr Val Thr Ile Val Leu Gly
225                 230                 235                 240

Val Phe Ile Val Cys Trp Leu Pro Ala Phe Ser Ile Leu Leu Leu Asp
                245                 250                 255

Tyr Ala Cys Pro Val His Ser Cys Pro Ile Leu Tyr Lys Ala His Tyr
            260                 265                 270

Phe Phe Ala Val Ser Thr Leu Asn Ser Leu Leu Asn Pro Val Ile Tyr
        275                 280                 285

Thr Trp Arg Ser Arg Asp Leu Arg Arg Glu Val Leu Arg Pro Leu Gln
    290                 295                 300

Cys Trp Arg Pro Gly Val Gly Val Gln Gly Arg Arg Arg Val Gly Thr
305                 310                 315                 320

Pro Gly His His Leu Leu Pro Leu Arg Ser Ser Ser Leu Glu Arg
                325                 330                 335

Gly Met His Met Pro Thr Ser Pro Thr Phe Leu Glu Gly Asn Thr Val
            340                 345                 350

Val

<210> SEQ ID NO 34
<211> LENGTH: 384
<212> TYPE: PRT
<213> ORGANISM: Homo sapiens

<400> SEQUENCE: 34

Met Asn Ala Thr Gly Thr Pro Val Ala Pro Glu Ser Cys Gln Gln Leu
1               5                   10                  15

Ala Ala Gly Gly His Ser Arg Leu Ile Val Leu His Tyr Asn His Ser
                20                  25                  30

Gly Arg Leu Ala Gly Arg Gly Gly Pro Glu Asp Gly Gly Leu Gly Ala
            35                  40                  45

Leu Arg Gly Leu Ser Val Ala Ala Ser Cys Leu Val Val Leu Glu Asn
        50                  55                  60

Leu Leu Val Leu Ala Ala Ile Thr Ser His Met Arg Ser Arg Arg Trp
65                  70                  75                  80

Val Tyr Tyr Cys Leu Val Asn Ile Thr Leu Ser Asp Leu Leu Thr Gly
                85                  90                  95

Ala Ala Tyr Leu Ala Asn Val Leu Leu Ser Gly Ala Arg Thr Phe Arg
            100                 105                 110

Leu Ala Pro Ala Gln Trp Phe Leu Arg Glu Gly Leu Leu Phe Thr Ala
        115                 120                 125

Leu Ala Ala Ser Thr Phe Ser Leu Leu Phe Thr Ala Gly Glu Arg Phe
    130                 135                 140

Ala Thr Met Val Arg Pro Val Ala Glu Ser Gly Ala Thr Lys Thr Ser
145                 150                 155                 160

Arg Val Tyr Gly Phe Ile Gly Leu Cys Trp Leu Leu Ala Ala Leu Leu
                165                 170                 175

Gly Met Leu Pro Leu Leu Gly Trp Asn Cys Leu Cys Ala Phe Asp Arg
            180                 185                 190

Cys Ser Ser Leu Leu Pro Leu Tyr Ser Lys Arg Tyr Ile Leu Phe Cys
        195                 200                 205

```
Leu Val Ile Phe Ala Gly Val Leu Ala Thr Ile Met Gly Leu Tyr Gly
    210                 215                 220

Ala Ile Phe Arg Leu Val Gln Ala Ser Gly Gln Lys Ala Pro Arg Pro
225                 230                 235                 240

Ala Ala Arg Arg Lys Ala Arg Arg Leu Leu Lys Thr Val Leu Met Ile
                245                 250                 255

Leu Leu Ala Phe Leu Val Cys Trp Gly Pro Leu Phe Gly Leu Leu Leu
                260                 265                 270

Ala Asp Val Phe Gly Ser Asn Leu Trp Ala Gln Glu Tyr Leu Arg Gly
                275                 280                 285

Met Asp Trp Ile Leu Ala Leu Ala Val Leu Asn Ser Ala Val Asn Pro
    290                 295                 300

Ile Ile Tyr Ser Phe Arg Ser Arg Glu Val Cys Arg Ala Val Leu Ser
305                 310                 315                 320

Phe Leu Cys Cys Gly Cys Leu Arg Leu Gly Met Arg Gly Pro Gly Asp
                325                 330                 335

Cys Leu Ala Arg Ala Val Glu Ala His Ser Gly Ala Ser Thr Thr Asp
                340                 345                 350

Ser Ser Leu Arg Pro Arg Asp Ser Phe Arg Gly Ser Arg Ser Leu Ser
    355                 360                 365

Phe Arg Met Arg Glu Pro Leu Ser Ser Ile Ser Ser Val Arg Ser Ile
    370                 375                 380

<210> SEQ ID NO 35
<211> LENGTH: 353
<212> TYPE: PRT
<213> ORGANISM: Homo sapiens

<400> SEQUENCE: 35

Met Asn Glu Cys His Tyr Asp Lys His Met Asp Phe Phe Tyr Asn Arg
1               5                   10                  15

Ser Asn Thr Asp Thr Val Asp Asp Trp Thr Gly Thr Lys Leu Val Ile
                20                  25                  30

Val Leu Cys Val Gly Thr Phe Phe Cys Leu Phe Ile Phe Phe Ser Asn
                35                  40                  45

Ser Leu Val Ile Ala Ala Val Ile Lys Asn Arg Lys Phe His Phe Pro
        50                  55                  60

Phe Tyr Tyr Leu Leu Ala Asn Leu Ala Ala Asp Phe Phe Ala Gly
65                  70                  75                  80

Ile Ala Tyr Val Phe Leu Met Phe Asn Thr Gly Pro Val Ser Lys Thr
                85                  90                  95

Leu Thr Val Asn Arg Trp Phe Leu Arg Gln Gly Leu Leu Asp Ser Ser
                100                 105                 110

Leu Thr Ala Ser Leu Thr Asn Leu Leu Val Ile Ala Val Glu Arg His
                115                 120                 125

Met Ser Ile Met Arg Met Arg Val His Ser Asn Leu Thr Lys Lys Arg
    130                 135                 140

Val Thr Leu Leu Ile Leu Leu Val Trp Ala Ile Ala Ile Phe Met Gly
145                 150                 155                 160

Ala Val Pro Thr Leu Gly Trp Asn Cys Leu Cys Asn Ile Ser Ala Cys
                165                 170                 175

Ser Ser Leu Ala Pro Ile Tyr Ser Arg Ser Tyr Leu Val Phe Trp Thr
                180                 185                 190

Val Ser Asn Leu Met Ala Phe Leu Ile Met Val Val Val Tyr Leu Arg
```

```
                195                 200                 205
Ile Tyr Val Tyr Val Lys Arg Lys Thr Asn Val Leu Ser Pro His Thr
    210                 215                 220

Ser Gly Ser Ile Ser Arg Arg Thr Pro Met Lys Leu Met Lys Thr
225                 230                 235                 240

Val Met Thr Val Leu Gly Ala Phe Val Cys Trp Thr Pro Gly Leu
                245                 250                 255

Val Val Leu Leu Leu Asp Gly Leu Asn Cys Arg Gln Cys Gly Val Gln
                260                 265                 270

His Val Lys Arg Trp Phe Leu Leu Ala Leu Leu Asn Ser Val Val
    275                 280                 285

Asn Pro Ile Ile Tyr Ser Tyr Lys Asp Glu Asp Met Tyr Gly Thr Met
    290                 295                 300

Lys Lys Met Ile Cys Cys Phe Ser Gln Glu Asn Pro Glu Arg Arg Pro
305                 310                 315                 320

Ser Arg Ile Pro Ser Thr Val Leu Ser Arg Ser Asp Thr Gly Ser Gln
                325                 330                 335

Tyr Ile Glu Asp Ser Ile Ser Gln Gly Ala Val Cys Asn Lys Ser Thr
                340                 345                 350

Ser

<210> SEQ ID NO 36
<211> LENGTH: 398
<212> TYPE: PRT
<213> ORGANISM: Homo sapiens

<400> SEQUENCE: 36

Met Glu Ser Gly Leu Leu Arg Pro Ala Pro Val Ser Glu Val Ile Val
1               5                   10                  15

Leu His Tyr Asn Tyr Thr Gly Lys Leu Arg Gly Ala Arg Tyr Gln Pro
                20                  25                  30

Gly Ala Gly Leu Arg Ala Asp Ala Val Val Cys Leu Ala Val Cys Ala
            35                  40                  45

Phe Ile Val Leu Glu Asn Leu Ala Val Leu Leu Val Leu Gly Arg His
        50                  55                  60

Pro Arg Phe His Ala Pro Met Phe Leu Leu Leu Gly Ser Leu Thr Leu
65                  70                  75                  80

Ser Asp Leu Leu Ala Gly Ala Ala Tyr Ala Ala Asn Ile Leu Leu Ser
                85                  90                  95

Gly Pro Leu Thr Leu Lys Leu Ser Pro Ala Leu Trp Phe Ala Arg Glu
            100                 105                 110

Gly Gly Val Phe Val Ala Leu Thr Ala Ser Val Leu Ser Leu Leu Ala
        115                 120                 125

Ile Ala Leu Glu Arg Ser Leu Thr Met Ala Arg Arg Gly Pro Ala Pro
    130                 135                 140

Val Ser Ser Arg Gly Arg Thr Leu Ala Met Ala Ala Ala Trp Gly
145                 150                 155                 160

Val Ser Leu Leu Leu Gly Leu Leu Pro Ala Leu Gly Trp Asn Cys Leu
                165                 170                 175

Gly Arg Leu Asp Ala Cys Ser Thr Val Leu Pro Leu Tyr Ala Lys Ala
            180                 185                 190

Tyr Val Leu Phe Cys Val Leu Ala Phe Val Gly Ile Leu Ala Ala Ile
        195                 200                 205

Cys Ala Leu Tyr Ala Arg Ile Tyr Cys Gln Val Arg Ala Asn Ala Arg
```

-continued

```
            210                 215                 220
Arg Leu Pro Ala Arg Pro Gly Thr Ala Gly Thr Thr Ser Thr Arg Ala
225                 230                 235                 240

Arg Arg Lys Pro Arg Ser Leu Ala Leu Leu Arg Thr Leu Ser Val Val
                245                 250                 255

Leu Leu Ala Phe Val Ala Cys Trp Gly Pro Leu Phe Leu Leu Leu Leu
            260                 265                 270

Leu Asp Val Ala Cys Pro Ala Arg Thr Cys Pro Val Leu Leu Gln Ala
        275                 280                 285

Asp Pro Phe Leu Gly Leu Ala Met Ala Asn Ser Leu Leu Asn Pro Ile
    290                 295                 300

Ile Tyr Thr Leu Thr Asn Arg Asp Leu Arg His Ala Leu Leu Arg Leu
305                 310                 315                 320

Val Cys Cys Gly Arg His Ser Cys Gly Arg Asp Pro Ser Gly Ser Gln
                325                 330                 335

Gln Ser Ala Ser Ala Ala Glu Ala Ser Gly Gly Leu Arg Arg Cys Leu
            340                 345                 350

Pro Pro Gly Leu Asp Gly Ser Phe Ser Gly Ser Glu Arg Ser Ser Pro
        355                 360                 365

Gln Arg Asp Gly Leu Asp Thr Ser Gly Ser Thr Gly Ser Pro Gly Ala
    370                 375                 380

Pro Thr Ala Ala Arg Thr Leu Val Ser Glu Pro Ala Ala Asp
385                 390                 395
```

<210> SEQ ID NO 37
<211> LENGTH: 372
<212> TYPE: PRT
<213> ORGANISM: Artificial Sequence
<220> FEATURE:
<223> OTHER INFORMATION: Description of artificial sequence: Chimeric
      Edg receptor

<400> SEQUENCE: 37

```
Met Gly Ser Leu Tyr Ser Glu Tyr Leu Asn Pro Asn Lys Val Gln Glu
1               5                   10                  15

His Tyr Asn Tyr Thr Lys Glu Thr Leu Glu Thr Gln Glu Thr Thr Ser
                20                  25                  30

Arg Gln Val Ala Ser Ala Phe Ile Val Ile Leu Cys Cys Ala Ile Val
            35                  40                  45

Val Glu Asn Leu Leu Val Leu Ile Ala Val Ala Arg Asn Ser Lys Phe
        50                  55                  60

His Ser Ala Met Tyr Leu Phe Leu Gly Asn Leu Ala Ala Ser Asp Leu
65                  70                  75                  80

Leu Ala Gly Val Ala Phe Val Ala Asn Thr Leu Leu Ser Gly Ser Val
                85                  90                  95

Thr Leu Arg Leu Thr Pro Val Gln Trp Phe Ala Arg Glu Gly Ser Ala
            100                 105                 110

Ser Ile Thr Leu Ser Ala Ser Val Phe Ser Leu Leu Ala Ile Ala Ile
        115                 120                 125

Glu Arg His Val Ala Ile Ala Lys Val Lys Leu Tyr Gly Ser Asp Lys
    130                 135                 140

Ser Cys Arg Met Leu Leu Leu Ile Gly Ala Ser Trp Leu Ile Ser Leu
145                 150                 155                 160

Val Leu Gly Gly Leu Pro Ile Leu Gly Trp Asn Cys Leu Gly His Leu
                165                 170                 175
```

-continued

```
Glu Ala Cys Ser Thr Val Leu Pro Leu Tyr Ala Lys His Tyr Val Leu
            180                 185                 190

Cys Val Thr Ile Phe Ser Ile Leu Leu Ala Ile Val Ala Leu
        195                 200                 205

Tyr Val Arg Ile Tyr Cys Val Lys Ser Ser Arg Lys Val Ala
210                 215                 220

Asn His Asn Asn Ser Glu Arg Ser Met Ala Leu Leu Arg Thr Val Thr
225                 230                 235                 240

Ile Val Leu Gly Val Phe Ile Val Cys Trp Leu Pro Ala Phe Ser Ile
                245                 250                 255

Leu Leu Leu Asp Tyr Ala Cys Pro Val His Ser Cys Pro Ile Leu Tyr
            260                 265                 270

Lys Ala His Tyr Phe Phe Ala Val Ser Thr Leu Asn Ser Leu Leu Asn
        275                 280                 285

Pro Val Ile Tyr Thr Trp Ala Ser Lys Glu Met Arg Arg Ala Phe Phe
    290                 295                 300

Arg Leu Val Cys Asn Cys Leu Val Arg Gly Arg Gly Ala Arg Ala Ser
305                 310                 315                 320

Pro Ile Gln Pro Ala Leu Asp Pro Ser Arg Ser Lys Ser Ser Ser Ser
                325                 330                 335

Asn Asn Ser Ser His Ser Pro Lys Val Lys Glu Asp Leu Pro His Thr
            340                 345                 350

Asp Pro Ser Ser Cys Ile Met Asp Lys Asn Ala Ala Leu Gln Asn Gly
        355                 360                 365

Ile Phe Cys Asn
    370

<210> SEQ ID NO 38
<211> LENGTH: 393
<212> TYPE: PRT
<213> ORGANISM: Artificial Sequence
<220> FEATURE:
<223> OTHER INFORMATION: Description of artificial sequence:  Chimeric
      Edg receptor

<400> SEQUENCE: 38

Met Glu Ser Gly Leu Leu Arg Pro Ala Pro Val Ser Glu Val Ile Val
1               5                   10                  15

Leu His Tyr Asn Tyr Thr Gly Lys Leu Arg Gly Ala Arg Tyr Gln Pro
            20                  25                  30

Gly Ala Gly Leu Arg Ala Asp Ala Val Val Cys Leu Ala Val Cys Ala
        35                  40                  45

Phe Ile Val Leu Glu Asn Leu Ala Val Leu Leu Val Leu Gly Arg His
    50                  55                  60

Pro Arg Phe His Ala Pro Met Phe Leu Leu Leu Gly Ser Leu Thr Leu
65                  70                  75                  80

Ser Asp Leu Leu Ala Gly Ala Ala Tyr Ala Ala Asn Ile Leu Leu Ser
                85                  90                  95

Gly Pro Leu Thr Leu Lys Leu Ser Pro Ala Leu Trp Phe Ala Arg Glu
            100                 105                 110

Gly Gly Val Phe Val Ala Leu Thr Ala Ser Val Leu Ser Leu Leu Ala
        115                 120                 125

Ile Ala Leu Glu Arg Ser Leu Thr Met Ala Arg Arg Gly Pro Ala Pro
    130                 135                 140

Val Ser Ser Arg Gly Arg Thr Leu Ala Met Ala Ala Ala Ala Trp Gly
145                 150                 155                 160
```

```
Val Ser Leu Leu Leu Gly Leu Leu Pro Ala Leu Gly Trp Asn Cys Leu
            165                 170                 175

Gly Arg Leu Asp Ala Cys Ser Thr Val Leu Pro Leu Tyr Ala Lys Ala
            180                 185                 190

Tyr Val Leu Phe Cys Val Leu Ala Phe Val Gly Ile Leu Ala Ala Ile
        195                 200                 205

Cys Ala Leu Tyr Ala Arg Ile Tyr Cys Gln Val Arg Ala Asn Ala Arg
    210                 215                 220

Arg Leu Pro Ala Arg Pro Gly Thr Ala Gly Thr Thr Ser Thr Arg Ala
225             230                 235                 240

Arg Arg Lys Pro Arg Ser Leu Ala Leu Leu Arg Thr Leu Ser Val Val
            245                 250                 255

Leu Leu Ala Phe Val Ala Cys Trp Gly Pro Leu Phe Leu Leu Leu Leu
            260                 265                 270

Leu Asp Val Ala Cys Pro Ala Arg Thr Cys Pro Val Leu Leu Gln Ala
            275                 280                 285

Asp Pro Phe Leu Gly Leu Ala Met Ala Asn Ser Leu Leu Asn Pro Ile
    290                 295                 300

Ile Tyr Thr Leu Arg Asp Ala Glu Met Arg Arg Thr Phe Arg Arg Leu
305             310                 315                 320

Leu Cys Cys Ala Cys Leu Arg Gln Ser Thr Arg Glu Ser Val His Tyr
                325                 330                 335

Thr Ser Ser Ala Gln Gly Gly Ala Ser Thr Arg Ile Met Leu Pro Glu
            340                 345                 350

Asn Gly His Pro Leu Met Thr Pro Pro Phe Ser Tyr Leu Glu Leu Gln
        355                 360                 365

Arg Tyr Ala Ala Ser Asn Lys Ser Thr Ala Pro Asp Asp Leu Trp Val
    370                 375                 380

Leu Leu Ala Gln Pro Asn Gln Gln Asp
385             390
```